United States Patent [19]

Musho et al.

[11] Patent Number: 5,202,261

[45] Date of Patent: Apr. 13, 1993

[54] CONDUCTIVE SENSORS AND THEIR USE IN DIAGNOSTIC ASSAYS

[75] Inventors: Matthew K. Musho, Elkhart; J. Oakey Noell; Pius H. Tse, both of Mishawaka, all of Ind.

[73] Assignee: Miles Inc., Elkhart, Ind.

[21] Appl. No.: 793,180

[22] Filed: Nov. 18, 1991

Related U.S. Application Data

[63] Continuation of Ser. No. 554,393, Jul. 19, 1990, abandoned.

[51] Int. Cl.$^5$ .................... C12M 1/40; C12M 1/34; G01N 27/26
[52] U.S. Cl. .................... 435/288; 435/291; 435/817; 204/403
[58] Field of Search .................... 435/288, 291, 817; 204/403

[56] References Cited

U.S. PATENT DOCUMENTS

| | | | |
|---|---|---|---|
| 3,632,483 | 1/1972 | Baum | 435/288 |
| 4,552,840 | 11/1985 | Riffer | 435/288 |
| 4,560,534 | 12/1985 | Kung et al. | 422/68 |
| 4,689,309 | 8/1987 | Jones | 422/56 |
| 4,721,677 | 1/1988 | Clark, Jr. | 435/288 |
| 4,795,707 | 1/1989 | Niiyama et al. | 435/288 |
| 4,927,516 | 5/1990 | Yanaguchi et al. | 435/288 |

Primary Examiner—Robert J. Warden
Assistant Examiner—T. A. Trembley
Attorney, Agent, or Firm—Roger N. Coe; Jerome L. Jeffers

[57] ABSTRACT

A conductive sensor and its use in a diagnostic assay are disclosed. The miniaturized conductive sensor, utilizing a conducting polymer, is used in a diagnostic device to determine the presence or concentration of a predetermined analyte in a liquid test sample, wherein the predetermined analyte, like glucose, is assayed by an oxidase interaction. The interaction between the oxidase and a small amount of the predetermined analyte in the test sample generates, either directly or indirectly, a dopant compound in a reaction zone of the conductive sensor. The dopant compound then migrates to the detection zone of the conductive sensor of the diagnostic device to oxidize the conducting polymer and convert the conducting polymer from an insulating form to a conducting form. The resulting increase in conductivity of the conducting polymer is measured, then the conductivity increase is correlated to the concentration of the predetermined analyte in the test sample.

21 Claims, 9 Drawing Sheets

CONDUCTIVE SENSORS AND THEIR USE IN DIAGNOSTIC ASSAYS

This is a continuation, of application Ser. No. 554,393, filed Jul. 19, 1990, now abandoned.

FIELD OF INVENTION

The present invention relates to a method of determining the presence or concentration of a predetermined analyte in a test sample with a diagnostic device including a miniaturized conductive sensor. The conductive sensor comprising a reaction zone including an enzyme that selectively interacts with the predetermined analyte and a detection zone including a layer or film of a conducting polymer and a microelectrode assembly. More particularly, a diagnostic device is employed to selectively assay a test sample for the presence or concentration of a specific predetermined analyte by measuring the change in conductivity of a layer of conducting polymer present in the detection zone of the conductive sensor. The conductivity change of the layer of conducting polymer results from the generation of a dopant compound in the reaction zone of the sensor due, either directly or indirectly, to an enzymatic interaction with the predetermined analyte. The dopant compound then migrates from the reaction zone of the sensor to the detection zone of the conductive sensor to dope the layer of conducting polymer and change the conductivity of the polymer. For example, a dopant compound, molecular iodine, is formed in the reaction zone in a reaction between iodide ions, a peroxidase enzyme or a molybdenum(VI) transition metal catalyst; and the hydrogen peroxide formed from a glucose oxidase interaction with glucose. The dopant compound then migrates, or diffuses, from the reaction zone to dope, oxidatively, the layer of conducting polymer in the detection zone. Surprisingly and unexpectedly, the configuration of the conductive sensor is such that only a small fraction of the glucose in the test sample, such as about 1% or less, is enzymatically converted to generate the dopant compound. Accordingly, oxygen limitations in the enzyme interaction are avoided. However, the amount of a generated dopant compound is sufficient to change the conductivity of the conducting polymer layer in the conductive sensor and allow an accurate conductivity measurement that can be correlated to the amount of the glucose in the test sample.

BACKGROUND OF THE INVENTION AND PRIOR ART

Reagent-impregnated test strips are commercially-available for a variety of predetermined analytes, such as glucose. These test strips are accurate, economical and relatively easy-to-use by an individual at home. The availability of such test strips has played a major role in the decentralization of the diagnostic market and has played an especially critical role in the development of home blood glucose monitoring that enables better glycemic control for diabetic individuals. In addition, other analyte detection devices designed for home use and that utilize amperometric, electrochemical detection of the predetermined analyte also are available. However, two important limitations remain in currently available technologies for home monitoring of a predetermined analyte, including the sample volume and the length of time that the assay requires. Generally, a test sample volume of between 5 $\mu$L and 20 $\mu$L (microliters) is required to perform an assay. The test sample is obtained by a finger puncture that produces fresh capillary blood. This is a relatively painful procedure, and the discomfort involved affects the willingness of an individual to perform assays as often as medically useful. In addition, currently-available assays require between 30 seconds and two minutes to complete.

Investigators have therefore shown an intense interest in developing electrochemical sensors that can be miniaturized, and therefore either be implanted subcutaneously or require a much smaller sample volume. Numerous approaches have been tried, including amperometric sensors based upon fiber electrodes and potentiometric sensors manufactured using techniques established in the semi-conductor industry. In contrast, the present invention measures a conductivity change in a thin polymer film, and accordingly has solved many of the problems inherent in miniaturized electrochemical sensors. Most importantly, an electrochemical sensor of the present invention can be manufactured in a planar format, using semi-conductor technologies, to provide an economical, disposable sensing element. Also, the sensor can be made sufficiently small such that a sample volume of 1 $\mu$L or less can be assayed. The sensitivity of the detection method also has solved the general oxygen limitation problem frequently observed in electrochemical sensors that utilize oxidase enzymes. Therefore, in accordance with an important feature of the present invention, an electrochemical sensor that can be miniaturized; that provides rapid and accurate assays; that overcomes oxygen limitation problems; that is free of interferences attributed to common constituents in the test sample; and that can be produced economically is achieved.

In general, a diagnostic device of the present invention comprises a reaction zone wherein the predetermined analyte of interest interacts with a suitable oxidase enzyme to generate, either directly or indirectly, a dopant compound. The dopant compound is capable of oxidizing a conducting polymer to change the conductivity of the polymer. In addition, the diagnostic device further comprises a detection zone including a film or layer of conducting polymer and a microelectrode assembly. The change in conductivity of the conducting polymer layer as a result of the dopant compound is detected or measured by the microelectrode assembly. The change in conductivity then is correlated to the amount of predetermined analyte in the test sample. As will be demonstrated more fully hereinafter, an economical and reproducible conductive sensor, useful in assaying for a predetermined analyte that responds to oxidase chemistry, has been provided. The conductive sensor utilizes the properties of conducting polymers, avoids oxygen limitation problems in the normal concentration ranges of the predetermined analyte; can be manufactured by well-known semiconductor processing techniques; and does not rely upon a chemical reaction occurring at the microelectrode assembly.

Accordingly, one important feature of the conductive sensor of the present invention is the conducting polymer included in the detection zone of the conductive sensor. Several organic conducting polymers, such as polyacetylene, polypyrrole and polythiophene, are known. The organic conducting polymers have several potential applications in the fields of batteries, display devices, corrosion prevention in metals and semiconductors and in microelectronic devices such as diodes, transistors, sensors, light emitting devices and energy conversion and storage elements. However, organic conducting polymers possess several limitations that have hindered the use of organic conducting polymers in conductive sensors. In general, a conducting polymer useful in the conductive sensor of the present invention should display a sufficiently high conductivity for detectable and accurate measurements, and should be capable of being processed, reproducibly, into thin, uniform films. Although several conducting polymers possess one of these two necessary properties, only a limited number of conducting polymers possess both necessary properties.

For example, polyacetylene acts as an insulator exhibiting conductivities in the range of $10^{-10}$ S/cm to $10^{-13}$ S/cm (Siemens per centimeter). A conductivity in this range corresponds to the conductivity of known insulators, such as glass and DNA. However, polyacetylene can be doped using a variety of oxidizing or reducing agents, such as antimony pentafluoride, the halogens, arsenic pentafluoride or aluminum chloride. By doping, polyacetylene is converted into a highly-conducting polymer exhibiting a conductivity of approximately $10^3$ S/cm, corresponding to the conductivity of metals such as bismuth.

However, polyacetylene suffers from the drawbacks of extreme instability in air and a sharp drop in conductivity when an alkyl or other substituent group is introduced into the polymer. Accordingly, the instability of polyacetylene in the presence of oxygen, and the inability of substituted polyacetylenes to maintain a high conductivity, generally makes polyacetylene unsuitable as the conducting polymer in a conductive analyte sensor. As will be discussed more fully hereinafter, conducting polymers including alkyl or other substituent groups usually possess physical and mechanical properties making the substituted conducting polymer more easily processible into conducting polymeric films than the corresponding unsubstituted conducting polymer. Therefore, in the manufacture of conductive sensors it is desirable to use an easy-to-process conducting polymer, such as a conducting polymer that is stable in air and possesses suitable mechanical and physical properties, like solubility in organic solvents.

Similarly, the conducting polymer polypyrrole exhibits conductivities ranging from about 1 S/cm to about 100 S/cm. Investigators again found that placing substituent groups on either the nitrogen atom or a carbon atom of the heteroaromatic pyrrole ring decreases the conductivity of polypyrrole. For example, an unsubstituted polypyrrole, incorporating the tetrafluoroborate anion as the dopant compound, exhibits a conductivity of 40 S/cm, whereas the N-methyl derivative, incorporating the same dopant compound, exhibits a conductivity of $10^{-3}$ S/cm; the three-methyl derivative of pyrrole exhibits a conductivity of 4 S/cm; the 3,4-dimethyl derivative, a conductivity of 10 S/cm; and the 3,4-diphenyl derivative, a conductivity of $10^{-3}$ S/cm. Accordingly, substituted polypyrroles, although often demonstrating good physical properties, may not demonstrate a sufficient conductivity for use as the conducting polymer in a conductive analyte sensor.

As illustrated by the large conductivity drop in polypyrroles having substituents positioned on the pyrrole ring, even substituents as small as a methyl group introduce steric interactions sufficient to essentially destroy the conductivity of the polymer. However, as will be discussed more fully hereinafter, if a conducting polymer has a suitable substituent group present on the monomer units, reproducible processing of the conducting polymer into a thin film of uniform thickness is facilitated. Therefore, it would be desirable to provide a conductive sensor including a conducting polymer that is easy to process and that also exhibits a sufficiently high conductivity for sensitive and accurate analyte determinations.

The inability to add a substituent to a polypyrrole without significantly reducing the conductivity of the polymer is critical from a perspective of polymer processing. Polypyrrole and presently-known polypyrrole derivatives are intractable polymers that are insoluble in common organic solvents. Therefore, a polypyrrole cannot be processed conveniently. However, if a polypyrrole can be substituted without adversely affecting the electrical properties of the polymer, a processible polypyrrole may be developed.

The synthesis and conductivities of polypyrrole and substituted polypyrroles have been investigated extensively. The general references cited below include the information discussed above and further general information concerning polypyrroles. The representative references discussing the polypyrroles include:

M. S. Wrighton, *Science* 231, 32 (1986);

A. F. Diaz et al., *J. Electroanal. Chem.* 133, 233 (1982);

M. V. Rosenthal et al., *J. Electroanal. Chem. and Interfac. Chem.* 1, 297 (1985);

G. Bidan et al., *Synth Met.* 15, 51 (1986);

E. M. Genies et al., *Synth. Met.* 10, 27 (1984/85); and

J. P. Travers et al., *Mol. Cryst. Liq. Cryst.* 118, 149 (1985).

Investigators also have found that steric interactions in substituted polythiophenes are somewhat less dominant than those observed in substituted polypyrroles because the predominant destabilizing interactions in substituted pyrroles involve the hydrogen atom of the pyrrole nitrogen. These steric interactions are absent in the polythiophenes, and therefore, electronic effects are more predominant in substituted polythiophenes.

Polythiophene also is a well-studied, stable conducting polymer. Polythiophene resembles polypyrrole in that polythiophene can be cyclized between its conducting, i.e. oxidized, state and its nonconducting, i.e. neutral, state without significant chemical decomposition of the polymer and without appreciable degradation of the physical properties of the polymer. Polythiophene, like polypyrrole, exhibits conductivity changes in response both to the amount of dopant compound and to the specific dopant compound, such as molecular iodine, iridium chloride, arsenic(III) fluoride, phosphorus(V) fluoride, perchlorate, tetrafluoroborate, hexafluorophosphate, hydrogen sulfate, hexafluoroarsenate and trifluoromethylsulfonate.

Substituents placed on the heteroaromatic thiophene ring can affect the resulting conducting polymer. However, in contrast to pyrrole, ring substituents on thiophene do not seriously reduce the conductivity of the resulting heteroaromatic polymer. For example, it has been found that for 3-methylthiophene and 3,4-dimethylthiophene, the resulting substituted polythiophene exhibited an improved conductivity compared to the unsubstituted parent polythiophene, presumably due to enhanced order in the polymer chain of the substituted thiophene. Accordingly, unlike many pyrroles, substituents can be included on the thiophene monomer units to improve the processing properties of the resulting conducting polymer without adversely affecting the conductivity of the conducting polymer. Therefore, as a class, substituted polythiophenes are well-suited for use as the conducting polymers in a conductive analyte sensor.

The following are representative publications describing the synthesis and conductivity of polythiophene, substituted polythiophenes and the related poly(thienylene vinylenes):

G. Tourillon, "Handbook of Conducting Polymers," T. A. Skotheim, ed., Marcel Dekker, Inc., New York, 1986, p. 293;

R. J. Waltham et al., *J. Phys. Chem.* 87, 1459 (1983);

G. Tourillon et al., *J. Polym. Sci. Polym. Phys. Ed.* 22, 33 (1984);

G. Tourillon et al., *J. Electroanal. Chem.* 161, 51 (1984);

A. F. Diaz and J. Bargon, "Handbook of Conducting Polymers," T. A. Skotheim, ed., Marcel Dekker, Inc., New York 1986, p. 81;

G Tourillon et al., *J. Phys. Chem.* 87, 2289 (1983);

A. Czerwinski et al., *J. Electrochem. Soc.* 132, 2669 (1985);

K. Jen et al., *J. Chem. Soc., Chem. Commun.*, 215 (1988); and

R. L. Elsenbaumer et al., *Electronic Properties of Conjugated Polymers*, 400 (1987).

From the studies on the polyacetylenes, polypyrroles and polythiophenes, and from related studies on other conducting polymers, it became apparent that a balance exists between the electronic effects and the steric effects introduced by the substituent on the monomer unit that renders a polymer of a substituted five or six member heteroaromatic ring more conducting or less conducting than the unsubstituted parent heteroaromatic compound. Therefore, it would be advantageous to utilize a conducting polymer having sufficient conductivity and suitable processing properties, such that the polymer can be used in a sensitive conductive analyte sensor of a diagnostic device to accurately determine the presence or concentration of a predetermined analyte in a liquid test sample.

Accordingly, the present invention is directed to a conductive sensor useful in a diagnostic assay for a predetermined analyte. More specifically, the conductive sensor is used in a diagnostic device to determine the presence or concentration of a predetermined analyte, like glucose, that is capable of interacting with an oxidase enzyme. The predetermined analyte and the oxidase interact in a reaction zone of the conductive sensor to generate, either directly or indirectly, a dopant compound. The dopant compound then migrates to a detection zone of the conductive sensor to oxidatively dope a layer or film of conducting polymer, thereby altering the conductivity of the layer of conducting polymer. The change in conductivity of the conducting polymer then is detected or measured by a microelectrode assembly, and can be correlated to the concentration of the predetermined analyte in the test sample.

The prior art includes teachings related to diagnostic assays using conducting polymers. However, the known prior art does not include any references suggesting or anticipating the miniaturized conductive sensor of the present invention, or its method of use. Furthermore, although several references disclose the use of conducting organic polymers in sensors, no known prior art reference discloses a sensor demonstrating the sensitivity and accuracy of the conductive sensor of the present invention. The prior art sensors are based upon a direct interaction of an analyte, usually a gas, with the conducting polymer. In contrast, the present conductive sensors utilize a response to a dopant compound generated, either directly or indirectly, by an interaction between the predetermined analyte and an oxidase enzyme. The dopant compound then migrates, or diffuses, into the layer of conducting polymer and alters the conductivity of the layer of conducting polymer, thereby allowing the determination of the presence or concentration of the predetermined analyte in the test sample.

The observed sensitivity of the conducting polymer to the concentration of the dopant compound is important in the development of sensors that are based upon oxidase enzymes. As will be demonstrated more fully hereinafter, a very small amount of the dopant compound generates a response. Therefore, only a small fraction of the available predetermined analyte in the test sample, such as less than 1% of the available analyte, is interacted and converted into the dopant molecule. As a result, the problem of an oxygen limitation, inherent in using oxidase enzymes, is overcome, and a sensitive determination of the total analyte concentration in the test sample is achieved.

The most common mode of interaction between an analyte and a conducting polymer is to affect the state of oxidation of the organic conducting polymer. As will be discussed more fully in the detailed description of the invention, the conductivity of the conducting polymer is related to the degree of oxidation of the conducting polymer, with the degree of oxidation, in turn related to the amount of dopant compound doping the conducting polymer. Therefore, the measured change in conductivity of the conducting polymer is correlated to the amount of dopant compound oxidizing the conducting polymer. In accordance with the method of the present invention, the amount of dopant compound in the layer of conducting polymer is directly related to the amount of predetermined analyte in the test sample. Consequently, a measurement of the rate of conductivity change of the layer of conducting polymer also is a measurement of the concentration of the predetermined analyte in the test sample.

For example, M. K. Malmros et al., in the publication, "A Semiconductive Polymer Film Sensor for Glucose", *Biosensors* 3, pp. 71-87 (1987/88), suggest using polyacetylene in a biosensor to quantitatively detect glucose. Malmros et al. teach the conversion of glucose by glucose oxidase to gluconic acid and hydrogen peroxide, and the subsequent conversion of iodide ion to molecular iodine, or triiodide anion, by the action of lactoperoxidase. Malmros et al. further teach that the iodine so generated can be used to change the conductivity of a polyacetylene film, particularly as a modifier of the effect of the peroxide.

Malmros et al. however do not teach a biosensor that solves the problems of assay interference and of oxygen limitation due to the low oxygen concentrations in biological samples. Malmros et al. teach the physical effect of the enzymatically generated iodine doping the polyacetylene polymer. The iodine is generated in solution through the addition of solution phase enzyme. Malmros et al. do not teach the incorporation of the enzymes or the iodide ion into solid phase films that can be laminated onto a conducting polymer film. Similarly, Malmros et al. do not teach a means of metering the test sample through a diffusion barrier or measuring the early kinetics of the reaction.

Moreover, the method disclosed by Malmros et al. cannot be employed in a biosensor due to the inherent limitations of the polyacetylene film. Most importantly, a polyacetylene cannot be processed using either solution casting or low temperature melt processes. As a result, thin polyacetylene films, such as 200 Å in thickness, cannot be produced. A thick film of conducting polymer greatly reduces the sensitivity of the film to a dopant compound by requiring more dopant compound to achieve the same level of doping. This in turn increases the amount of predetermined analyte in the sample that must be converted into iodine to achieve a response. As will be demonstrated more fully hereinafter, the ability to cast thin films of the conducting polymer is an important aspect in providing reliable and accurate assay results.

Similarly, Malmros et al., in European Patent Application Publication No. 096,095, disclose an immunoassay utilizing doped conducting polymers, wherein the resistance of the polymer varies in response to the analyte in solution. Although Malmros et al. utilize a polyacetylene conducting polymer in an immunosensor, Malmros et al. do not teach or suggest assaying for a predetermined analyte capable of interacting with an oxidase enzyme to, either directly or indirectly, produce a dopant compound such that the rate of the conductivity change of the conducting polymer as the dopant compound oxidizes the conducting polymer is correlated to the concentration of the predetermined analyte in the test sample.

Wrighton et al., in European Patent Application Publication No. 185,941, disclose the use of conducting organic polymers as the active species in a chemical sensor. Wrighton et al. generally teach using the changes in physical properties of the conducting polymer as the active transduction into electrical signals. Specific examples cited in the patent include detection of oxygen gas, hydrogen gas, pH and enzyme substrate concentrations like glucose. The principal transduction mechanism described by Wrighton et al. is the direct use of the change in polymer conductivity induced by oxidation or by reduction. In contrast to the present invention, Wrighton et al. include the reaction catalyst, like an enzyme, in the conducting polymer matrix. Accordingly, the interaction occurs within the conducting polymer matrix. In the device and method of the present invention, the entire analyte-oxidase interaction occurs essentially in a reaction zone of the device to generate the dopant compound; the dopant compound then migrates from the reaction zone to a detection zone that includes the layer of conducting polymer. The rate of change of conductivity of the conducting polymer layer as the dopant compound diffuses from the reaction zone to the detection zone is used to measure the concentration of the predetermined analyte in the test sample. Wrighton et al. do not teach a method of integrating the glucose oxidation by oxygen into the oxidation properties of the polymer, nor do Wrighton et al. teach the conversion of glucose to iodine through coupled enzymatic reactions. Furthermore, Wrighton et al. do not teach the use of solution processible polymers; all of the polymers used by Wrighton et al. are grown electrochemically.

Wrighton et al., in U.S. Pat. No. 4,717,673, disclose polymer-based microsensors produced by anodic deposition of a conducting polymer onto a gold or platinum electrode surface. Wrighton et al. in U.S. Pat. No. 4,721,601 disclose microelectronic devices having electrodes functionalized with conducting polymers having specific properties. The devices disclosed in each patent measure resistance changes of electrochemically-grown polymers on electrode arrays having intergap spacings of less than two microns.

Elsenbaumer et al., in the publication "Processible, Environmentally Stable, Highly Conductive Forms of Polythiophene", *Synth. Met.*, 18, pp. 277–282 (1987), describe a series of conducting poly(3-alkylthiophene) polymers having sufficient conductivity, stability, mechanical properties and processibility for a variety of applications. Jen et al., in the publication "Processible and Environmentally Stable Conducting Polymers", *Polymeric Material*, Vol. 13, pp. 79–84 (1985) also describe polythiophenes having good conductivity and mechanical properties.

Hotta et al., in "Novel Organosynthetic Routes to Polythiophene and Its Derivatives", *Synth. Met.*, 26, pp. 267–279 (1988) teach the synthesis of poly(3-alkylthiophene) polymers having long alkyl side chains. Such conducting polymers are soluble in common organic solvents, are processible into uniform films and, when doped, exhibit excellent conductivity. Yoshino et al. in the three publications:

"Preparation and Properties of Conducting Heterocyclic Polymer Films by Chemical Method", *Jpn. Journ. Appl. Phys.*, 23, pp. 2899–2900 (1984);

"Electrical and Optical Properties of Poly(3-alkylthiophene) in Liquid State", *Solid State Commun.*, 67, pp. 1119–1121 (1988); and "Absorption and Emission Spectral Changes in a Poly(3-alkylthiophene) Solution with Solvent and Temperature", *Jpn. Journ. Appl. Phys.*, 26, pp. L2046–L2048 (1987), describe the synthesis and properties of the conducting poly(3-alkylthiophene) polymers. Jen et al., in U.S. Pat. No. 4,711,742, disclose doped and undoped conducting polymers that can be solubilized in organic solvents, with the resulting solution used to form conducting polymer films, including films of a poly(3-alkylthiophene).

Nagy et al., in the publication "Enzyme Electrode for Glucose Based on an Iodide Membrane Sensor," *Analytica Chim. Acta.*, 66, pp. 443–455 (1973), describe the detection of glucose by potentiometrically monitoring the disappearance of iodide ion. Nagy et al. monitor the decrease in iodide activity at the electrode surface, whereas the present invention monitors the amount of a predetermined analyte in the test sample by measuring the rate of change of conductivity of the conducting polymer due to the generation of a dopant compound by an oxidase enzyme mediated interaction.

Mullen et al., in the publication, "Glucose Enzyme Electrode with Extended Linearity," *Analytica. Chem. Acta.*, 183, pp. 59–66 (1986), describe a hydrogen peroxide-detecting electrode to assay whole blood for glucose. Mullen et al. disclose positioning a silane-treated membrane over a reactive enzyme layer to remove interferents and to extend the linearity of the electrode response to glucose concentration in undiluted whole blood. Similarly, Vadgama, in European Patent Application Publication No. 204,468, discloses a membrane for an enzyme-based electrode sensor to increase the range of linearity of the sensor response to generated hydrogen peroxide.

Other references relating to membranes, in general, or the detection of glucose in a test sample in particular, include M. B. McDonell and P. M. Vadgama, "Membranes: Separation Principles and Sensing", *Selective*

*Electrode Rev.*, 11, pp. 17-67 (1989); L. C. Clark et al., "Long-lived Implanted Silastic Drum Glucose Sensors", *Trans. Am. Soc. Artif. Intern. Organs, Vol. XXXIV*, pp. 323-328 (1987); P. Vadgama et al., "The Glucose Enzyme Electrode: Is Simple Peroxide Detection at a Needle Sensor Acceptable?", in *Implantable Glucose Sensors - The State of the Art*, International Symposium, Reisensburg, pp. 20-22 (1987); P. Vadgama, "Diffusion Limited Enzyme Electrodes", *Anal. Uses of Immobilized Biological Compounds for Detection, Medical and Industrial Uses*, pp. 359-377 (1988); and W. H. Mullen et al., "Design of Enzyme Electrodes for Measurements in diluted Blood", *Analytical Proceedings*, 24, pp. 147-148 (1987). These references also describe improved methods of detecting hydrogen peroxide in the assay of blood for glucose.

In addition to the above, the following references are representative of the state of the art of electromechanical sensors using heteroaromatic polymers:

Y. Ikariyama et al., *Anal. Chem.*, 58, 1803 (1986);

C. Nylander et al., *Anal. Chem. Symp. Ser.*, 17, (Chem Sens) 159 (1983);

H. S. White et al., *J. Am Chem. Soc.*, 106, 5317 (1984);

G. P. Kittlesen et al., *J. Am. Chem. Soc.*, 106, 7389 (1984);

Malmros, U.S. Pat. No. 4,444,892, disclosing a device having an analyte specific binding substance immobilized onto a semiconductive polymer to allow detection of a specific analyte;

European Patent Application Publication No. 193,154, disclosing immunosensors comprising a polypyrrole or polythiophene film having an antigen or antibody bound thereto; and M. Umana and J. Waller, *Anal. Chem.*, 58, 2979 (1986) disclose the occlusion, or trapping, of an enzyme, glucose oxidase, by electropolymerizing pyrrole in the presence of the enzyme. The polypyrrole containing the occluded enzyme then can be used to detect glucose. However, the method of the present invention differs in two critical respects. First, the detection mechanism in the present invention detects a generated oxidative dopant. The polymer film initially is present in its reduced, nonconducting form, and becomes conductive only as the dopant compound is produced enzymatically. In the publication of Umana and Waller, the polymer film initially is conductive and that conductivity is modulated by the enzymatic activity of the enzyme, that is serving as a dopant, and also by the generated peroxide. The second critical difference is that, in the present invention, the oxidase enzyme is retained in a distinct reaction zone layer that is in contact with the conducting polymer film in a detection zone layer.

Investigators also have studied various other problems associated with electrochemical sensors. For example, one major problem encountered in assays based on oxidase chemistry is the limited amount of molecular oxygen present in the system. In an oxidase catalyzed reaction, the predetermined analyte reacts with an equimolar amount of molecular oxygen. When the supply of molecular oxygen is depleted, the reaction ceases regardless of the presence of the oxidase enzyme and unreacted analyte. If no further molecular oxygen can enter the system, an erroneously low assay for the predetermined analyte results. If molecular oxygen can diffuse into the system, the oxidase-catalyzed reaction will continue, although slowly, until all the analyte is consumed. In this case, an accurate analyte is achieved, but the time needed to achieve the accurate assay is impractically long.

Therefore, investigators have sought methods to overcome the problem of oxygen limitation. One method is to mediate the oxidase-catalyzed reaction with a species other than oxygen. In this method, a compound such as ferrocene, a ferrocene derivative, ferricyanide couples or tetrathiafulvalene/tetracyanoquinone is used as a replacement for molecular oxygen. These compounds perform in a manner similar to molecular oxygen and are included in a sufficient amount such that all of the predetermined analyte in the test sample is oxidized. This method was used in an amperometric probe and is described by Cass et al. in *Anal. Chem.*, 56, p. 607 (1984) and in *Biosensors, Instrumentation and Processing*, The World Biotech. Report, Vol. 1, Part 3, p. 125 (1987).

Another disclosed method of avoiding the oxygen limitation problem is to eliminate oxygen and oxygen substitutes altogether, and allow a direct electron transfer from the enzyme to the electrode. This method is disclosed by Y. Degani and A. Heller, *J. Phys. Chem.*, 91, 1285 (1987). Furthermore, Vadgama, in European Patent Application Publication No. 204,468, disclosed avoiding oxygen limitations by using a silane-treated membrane to restrict entry of the predetermined analyte into the reaction enzyme layer. In contrast, the device and method of the present invention avoid the oxygen limitation problem kinetically, that is by detecting and measuring the concentration of the predetermined analyte before oxygen limitations occur and by limiting the amount of the predetermined analyte that contacts the reaction zone including the oxidase enzyme and the limited amount of molecular oxygen.

Another problem encountered in the design of a conductive sensor is the effect of interfering compounds that often are present in a test sample, such as the presence of ascorbate ion in the assay of a biological fluid for glucose. Investigators have found that in amperometric probes, interference from relatively easily oxidized compounds, such as ascorbate ion, phenolics, uric acid, acetaminophen and salicylates, occurs because the interfering compound is oxidized at the anode. Investigators accordingly have attempted to eliminate the affect of these interfering compounds. A common technique is exemplified in the publication of C. J. McNeil, et al., *Biosensors*, 3, p. 199-209 (1987/88), wherein the electroactive species was functionalized to lower its oxidation potential and thereby eliminate the interference in an immunosensor. I. Hannig et al., in "Improved Blood Compatibility at a Glucose Enzyme Electrode Used for Extra Corporeal Monitoring", *Anal. Letters*, 19(3&4), pp. 461-478 (1986), attempted to eliminate the effects of interferents by utilizing a thick enzyme layer to convert a relatively large amount of the available glucose. The corresponding large response for glucose conversion essentially swamped the interferent response.

In contrast, the method and device of the present invention utilizes a conductometric detection and measurement. Accordingly, an extremely low voltage can be used. The voltage is much lower than the oxidation potential of the interfering compounds, and therefore the interfering compounds are not oxidized. In addition, in the present invention, all chemical interactions occur in the reaction zone of the conductive sensor. The molecular iodine is generated in the reaction zone and migrates to dope the conducting polymer in the detection zone. Therefore, no direct interference is possible at the electrode.

However, the generated molecular iodine dopant compound is capable of interacting with various serum components, like ascorbate. If a sufficient amount of the molecular iodine interacts with serum components rather than doping the polymer, interferences are observed. Therefore, the method of the present invention relies upon fast assays to minimize interfering reactions of the generated molecular iodine. This is accomplished by the configuration of the sensor of the present invention, comprising a thin reaction zone and a thin detection zone, such that the molecular iodine is generated near the conducting polymer to quickly dope the conducting polymer before significant interfering reactions can occur. Furthermore, in the preferred embodiment of the present invention, it will be demonstrated that a semipermeable membrane utilized to meter the test sample into the reaction zone also selectively screens interfering compounds from the test sample, and therefore precluding an interaction with the generated molecular iodine.

Therefore, the method of the present invention allows the accurate assay of a predetermined analyte that is responsive to oxidase chemistry. The method utilizes a diagnostic device that includes a conductive sensor, wherein the conductive sensor comprises a reaction zone and a detection zone. The reaction zone of the conductive sensor is a thin film including the reagents necessary to interact with the predetermined analyte and to generate a dopant compound. The detection zone includes a film or layer of a conducting polymer and a microelectrode assembly such that the dopant compound can migrate to the detection zone to dope the conducting polymer, and such that the resulting change in conductivity, detected and measured by the microelectrode assembly, can be correlated to the amount of predetermined analyte in the test sample. The conductive sensor overcomes the disadvantages demonstrated by the prior art sensors, and therefore provides sensitive, accurate and reproducible assays; provides a fast assay, such as within 30 seconds, and preferably within 10 seconds, from a small blood sample, such as from about 0.1 $\mu l$ to about 5 $\mu l$; eliminates the oxygen limitation problem associated with oxidase chemistry; eliminates the problems associated with interfering compounds present in the test sample; demonstrates excellent shelf stability; is economical and disposable; and is miniaturized and can be reproducibly manufactured by semiconductor processing techniques.

SUMMARY OF THE INVENTION

In brief, the present invention is directed to a diagnostic device including a conductive analyte sensor comprising a reaction zone and a detection zone, wherein the detection zone includes a conducting polymer and a microelectrode assembly. More particularly, the present invention is directed to a conductive sensor that allows the sensitive and accurate detection and measurement of a predetermined analyte in a liquid test sample, wherein the predetermined analyte is assayed by an oxidase interaction. In accordance with the method of the present invention, an interaction between the predetermined analyte and an oxidase enzyme occurs in the reaction zone of the conductive sensor to produce, either directly or indirectly, a dopant compound that migrates to the detection zone of the sensor. The detection zone of the device is in laminar contact with the reaction zone and includes a layer or film of conducting polymer that is oxidized by the dopant compound. Therefore, the conductivity of the conducting polymer layer is changed, and the change in conductivity of the conducting polymer layer is detected and measured by the microelectrode assembly and is correlated to the concentration of the predetermined analyte in the test sample.

The conductive sensors of the present invention utilize the unique electrical properties of conducting polymers to determine the presence and concentration of a predetermined analyte that is capable of interacting with a specific oxidase enzyme. In accordance with the method and device of the present invention, the conductive sensors include a layer of conducting polymer in a detection zone of the sensor. The conducting polymer is oxidized by a dopant compound generated, either directly or indirectly, as a result of an interaction between the predetermined analyte and an oxidase enzyme in a reaction zone of the sensor. The dopant compound migrates from the reaction zone to the detection zone of the device to oxidize the layer of conducting polymer. The conductivity of the polymer, therefore, is changed by the introduction of the dopant compound into the conducting polymer layer, and the measurable conductivity change is detected and measured by a microelectrode assembly in the detection zone and is correlated to the concentration of the predetermined analyte in the test sample.

For example, hydrogen peroxide is produced in the reaction of glucose oxidase with glucose in the presence of oxygen. Then, the hydrogen peroxide, in the presence of a peroxidase enzyme or a compound that exhibits peroxidase activity, like a molybdenum(VI) transition metal catalyst, can interact with iodide ions to generate molecular iodine. Each of these reactions is quantitative. Therefore, by measuring the amount of molecular iodine that is generated, the original amount of glucose can be determined. In addition, the generated molecular iodine is a dopant compound, and the concentration of molecular iodine can be determined from the change in conductivity of a conducting polymer doped by the molecular iodine. Accordingly, measuring the change, or the rate of change, in conductivity of the conducting polymer can be correlated to the concentration of glucose in solution.

Consequently, it has been demonstrated that the conductive sensor of the present invention allows an accurate and sensitive electrical transduction of an analyte-oxidase interaction, like a glucose-glucose oxidase interaction. In accordance with an important feature of the present invention, the sensitive and accurate detection of a predetermined analyte, like glucose, results from the effect of the ultimately generated dopant compound, like molecular iodine, upon the conductivity of a conducting polymer layer. This particular type of reaction and detection method is known in the art. However, to date, utilizing this reaction in a conductive sensor has not provided a sensitive and accurate assay for a predetermined analyte.

Therefore, and in accordance with the present invention, an interaction between a predetermined analyte and an oxidase enzyme, and a subsequent interaction between the generated hydrogen peroxide, a dopant compound precursor and a peroxidase enzyme or a compound that exhibits peroxidase activity to generate a dopant compound, like molecular iodine, occurs in a reaction zone of a conductive sensor of a diagnostic device. The dopant compound migrates from the reaction zone to contact and oxidatively dope a layer or film of conducting polymer present in a detection zone of the sensor. Consequently, the conductivity of the conducting polymer layer is changed, and the concentration of the predetermined analyte is determined from the change in conductivity of the conducting polymer by a microelectrode assembly in the detection layer. Thus, to provide an accurate and sensitive assay by eliminating oxygen limitation problems in the oxidase-based reaction, the change in conductivity of the conducting polymer layer in the conductive sensor is measured within about thirty seconds, and preferably within about 15 seconds, after the test sample contacts the reaction zone of the conductive sensor. To achieve the full advantage of the present invention, the change in conductivity is measured from about 5 seconds to about 10 seconds after the test sample contacts the reaction zone of the sensor.

Therefore, it is an object of the present invention to provide a method of determining the presence or concentration of a predetermined analyte in a liquid test sample by utilizing a diagnostic device including a conductive sensor comprising a reaction zone in contact with a detection zone. It also is an object of the present invention to provide a method of determining the concentration of a predetermined analyte in a liquid test sample wherein the predetermined analyte interacts with an oxidase enzyme in the reaction zone of the sensor to generate, either directly or indirectly, a dopant compound that oxidizes a layer or film of conducting polymer in the detection zone of the sensor and that changes the conductivity of the conducting polymer.

Another object of the present invention is to provide a method of determining the concentration of a predetermined analyte in a test sample from the interaction of the analyte with an oxidase enzyme to produce, either directly or indirectly, a dopant compound that oxidizes a conducting polymer, such that a detectable or measurable conductivity change occurs in the conducting polymer and thereby establishes the presence or concentration of the predetermined analyte in the test sample.

Another object of the present invention is to provide a method of determining the presence or concentration of a predetermined analyte in a liquid sample comprising contacting a diagnostic test device with the liquid sample, wherein the diagnostic test device includes a conductive sensor comprising a reaction zone, wherein a portion of the predetermined analyte interacts with an oxidase enzyme and other reagents, if necessary, to generate a dopant compound, and a detection zone in contact with the reagent zone, such that the dopant compound migrates to the detection zone to dope a layer of conducting polymer present in the detection zone and to cause a detectable or measurable change in the conductivity of the conducting polymer; measuring the change in conductivity of the layer of conducting polymer by a microelectrode assembly present in the detection zone; and correlating the change in conductivity of the layer of conducting polymer to the concentration of the predetermined analyte in the test sample.

Another object of the present invention is to provide a sensitive, miniaturized conductive sensor capable of assaying a sample volume in the range of 0.1 $\mu L$ to about 5 $\mu L$, and especially less than 1 $\mu L$, that accurately senses the presence or concentration of a predetermined analyte in a test sample, wherein the predetermined analyte is capable of interacting with an oxidase enzyme; that essentially eliminates the effects of interfering compounds present in the test sample; that eliminates the problem of oxygen limitation in the oxidase reaction; and that provides an assay result within 10 seconds.

Another object of the present invention is to provide a sensitive conductive sensor that accurately senses the presence or concentration of a predetermined analyte in a liquid test sample, wherein the predetermined analyte is capable of interacting with an oxidase enzyme, comprising: a) a reaction zone including a hydratable host matrix permeable to the predetermined analyte and having homogeneously incorporated therein a suitable oxidase enzyme, a peroxidase enzyme or a compound that exhibits peroxidase activity, and any other necessary reagents, like a dopant compound precursor, to generate a dopant compound, and wherein the predetermined analyte interacts with the oxidase enzyme, peroxidase and other reagents, if present, to generate, either directly or indirectly, the dopant compound; b) a detection zone in contact with the reaction zone including a layer or film of a conducting polymer in contact with a microelectrode assembly, such that the dopant compound generated in the reaction zone can migrate to and oxidatively dope the film or layer of the conducting polymer; and c) means operatively connected to the microelectrode assembly of the detection zone for measuring the conductivity of the conducting polymer.

Another object of the present invention is to provide a sensitive conductive sensor that accurately senses the presence or concentration of a predetermined analyte in a liquid test sample, wherein the predetermined analyte is capable of interacting with an oxidase enzyme, comprising: a) semipermeable membrane capable of effectively separating the cellular material and interfering components from the test sample while allowing the predetermined analyte to diffuse through the semipermeable membrane; b) a reaction zone including a hydratable host matrix permeable to the predetermined analyte and having homogeneously incorporated therein a suitable oxidase enzyme, a peroxidase enzyme or a compound capable of exhibiting peroxidase activity, and any other necessary reagents, like a dopant compound precursor, to generate a dopant compound, and wherein the predetermined analyte interacts with the oxidase enzyme, the peroxidase enzyme or a compound that exhibits peroxidase activity, and other reagents, if present, to generate, either directly or indirectly, the dopant compound; c) a detection zone in contact with the reaction zone including a layer or film of a conducting polymer in contact with a microelectrode assembly, such that the dopant compound generated in the reaction zone can migrate to and oxidatively dope the film or layer of the conducting polymer; and d) means operatively connected to the microelectrode assembly of the detection zone for measuring the conductivity of the conducting polymer.

Another object of the present invention is to provide an accurate and sensitive miniaturized conductive sensor for determining the presence or concentration of glucose in a liquid test sample of less than 1 $\mu L$ comprising a reaction zone wherein the hydratable host matrix is a polymer matrix, such as a gelatin matrix or a chitosan matrix, incorporating therein glucose oxidase, peroxidase and iodide ion to interact with the glucose and to generate molecular iodine as the dopant compound upon contact between the liquid test sample and the reaction zone.

Another object of the present invention is to provide an accurate and sensitive miniaturized conductive sensor for determining the presence or concentration of a predetermined analyte capable of interacting with an oxidase enzyme comprising a detection zone comprising a layer, such as a thin film, of a conducting polymer in contact with a microelectrode assembly capable of measuring resistances as high as about $10^9$ ohms.

BRIEF DESCRIPTION OF THE DRAWINGS

The above and other objects and advantages and novel features of the present invention will become apparent from the following detailed description of the invention illustrated in the accompanying figures demonstrating the accurate and sensitive analyte assays achieved by the conductive sensor of the present invention wherein.

DETAILED DESCRIPTION OF THE INVENTION

Figure 1:
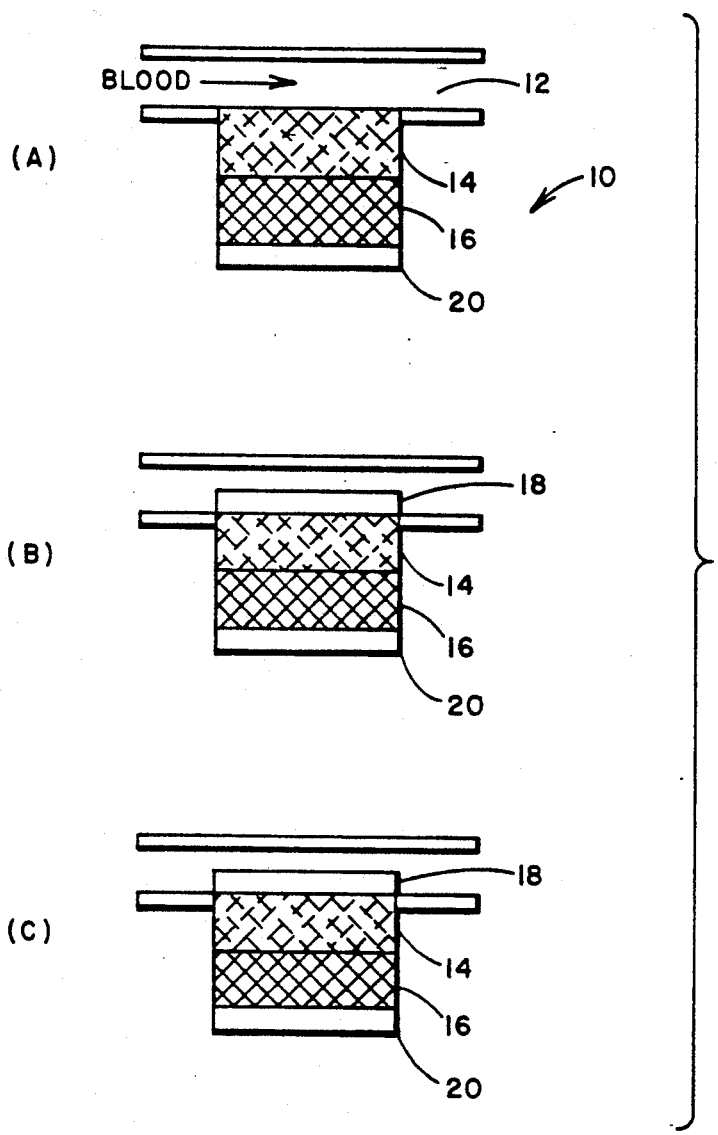
FIG. 1 is a partial side view in cross-section of a diagnostic device of the present invention comprising a capillary for introducing the test sample; and a conductive sensor comprising a reaction zone for interacting the predetermined analyte with an oxidase enzyme and for generating the dopant compound, and a detection zone for detecting the amount of dopant compound generated in the reaction zone by measuring the change in conductivity of a layer of conducting polymer present in the detection zone with a microelectrode assembly.

In accordance with the method and device of the present invention, a diagnostic device includes a conductive sensor comprising a reaction zone and a detection zone, wherein the detection zone includes a layer of a conducting polymer and a microelectrode assembly, to determine the presence or concentration of a predetermined analyte in a liquid test sample. Although conductive sensors have been studied extensively, the use of a conductive sensor in a diagnostic device to assay for a predetermined analyte, like glucose, has been impeded by several problems, including poor conducting polymer properties, impractical methods of manufacturing the conductive sensor, the inability to accurately test for a predetermined analyte, insensitivity to low concentrations of the predetermined analyte, irreproducible analyte assays, interferences associated with compounds often found in test samples, and oxygen limitation problems in assays based on oxidase chemistry. As will be described more fully hereinafter, the method and device of the present invention surprisingly and unexpectedly overcome many of the problems previous investigators encountered in attempts to incorporate a miniaturized conductive sensor into a diagnostic device.

In general, the conductive sensor of the present invention allows the detection and measurement, or monitoring, of a predetermined analyte in a liquid test sample. More specifically, an analyte capable of detection or measurement, either directly or indirectly, by an oxidase chemistry can be assayed by the conductive sensor of the present invention. For example, glucose, cholesterol, alcohol and other analytes capable of interacting with a suitable oxidase enzyme can be assayed by the method and device of the present invention. In addition, immunological analytes can be measured in competitive, displacement and sandwich ELISA formats by labelling with an appropriate oxidase enzyme. The method and device of the present invention are especially useful in the in vitro detection and measurement of glucose in a test sample. Accordingly, and as will be demonstrated more fully hereinafter, the method and device of the present invention provide more simple, more accurate and more sensitive analyte assays than prior art methods and devices utilizing conductive sensors.

Accordingly, the method and device of the present invention are based upon the oxidative doping of a conducting polymer, like a poly(3-alkylthiophene), present in the detection zone of the conductive sensor, by a dopant compound, such as molecular iodine, that is generated in the reaction zone of the sensor. As will be demonstrated more fully hereinafter, a poly(3-alkylthiophene), as depicted in structural formulas (I) (undoped) and (II) (doped), is a particularly useful conducting polymer in the method and device of the present invention. However, it should be understood that other conducting polymers demonstrating sufficient conductivity, i.e. detectable or measureable, and having sufficient stability, mechanical properties and processibility also are useful in the device and method of the present invention. For example, another class of conducting polymers exhibiting properties useful in the device and method of the present invention includes the poly(thienylene vinylene) polymers, depicted in general structural formula (III), and the related poly(furylene vinylene) polymers. A poly(thienylene vinylene) film doped with molecular iodine exhibited a conductivity of 62 S/cm, and a poly(furylene vinylene) film doped with molecular iodine exhibited a conductivity of 36 S/cm.

However, it has been difficult to provide a uniform, thin film of a conducting polymer. If a thin film of polymer is available, less dopant compound is needed to provide a detectable or measurable increase in conductivity. Surprisingly and unexpectedly, the conductive sensor and the method of the present invention provide a uniform, thin film of conducting polymer, such as from about 100 Å to about 1500 Å in thickness. Therefore, the sensitivity of the assay is increased because less dopant compound must be generated for a detectable response; and the accuracy of the assay is increased because the electrical response of a layer of the conducting polymer is increased, therefore making detec-

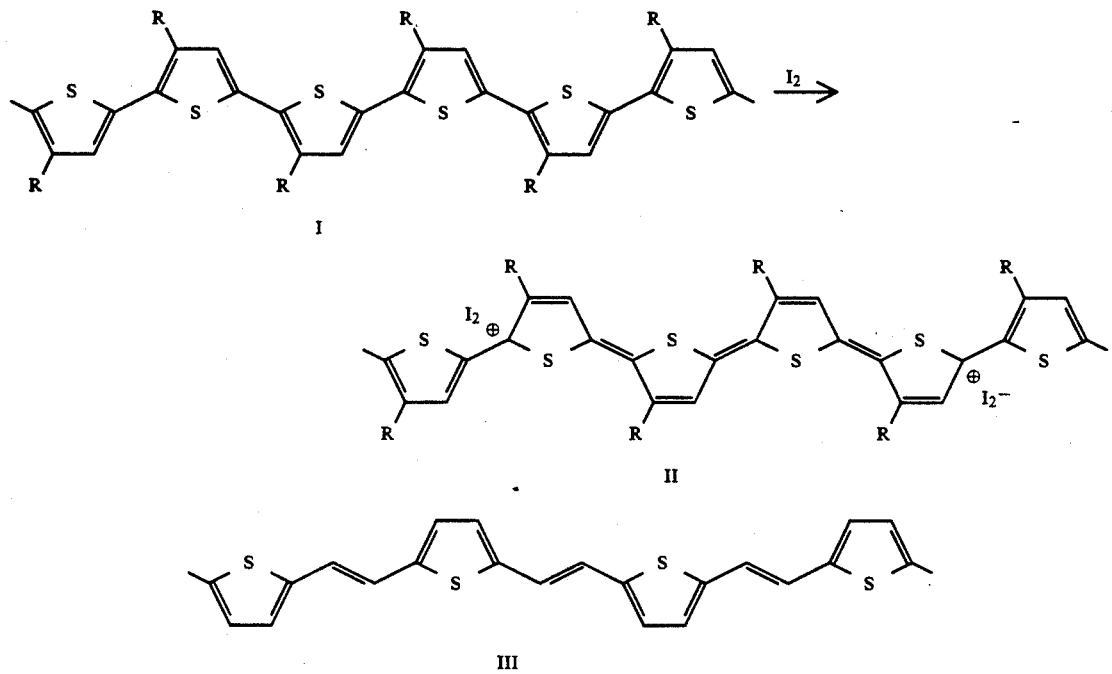

As previously discussed, the oxidized form of a conducting polymer, i.e. structure (II), demonstrates a dramatic increase in electrical conductivity compared to the reduced form of the conducting polymer, i.e. structure (I). For example, a conducting polymer in its completely reduced form is insulating, and exhibits a conductivity of about $10^{-7}$ S/cm. However, if the conducting polymer is fully oxidized, the conductivity can increase to as high as about $10^3$ S/cm, depending upon the chemical structure of the conducting polymer and the morphological condition of the conducting polymer layer. Furthermore, as disclosed by Burks and Hodge, in *J. Chem. Phys.*, 83, p. 5796 (1985), a conducting polymer requires approximately $10^{-11}$ moles of dopant compound per square centimeter of surface area of conducting polymer to demonstrate an order of magnitude change in the conductivity of a 200 Å (Angstrom) thick film of conducting polymer. Accordingly, this very sensitive conductivity response of the conducting polymer, especially a thin film of conducting polymer, to the concentration of the dopant compound doping the conducting polymer layer allows a conductive sensor of the present invention to provide sensitive and accurate assays for a predetermined analyte.

The increased conductivity of a conducting polymer upon oxidative doping by a dopant compound, such as molecular iodine or arsenic triflouride, is a well recognized electrical property of a conducting polymer.

tion measurements easier and more reliable. In addition, and as will be demonstrated more fully hereinafter, the ability to provide a thin, uniform layer of a conducting polymer helps eliminate the oxygen limitation problem found in oxidase-based assays. The sensitive detection provided by a thin film of conducting polymer allows a method wherein only a very minor portion of the analyte in the test sample interacts with the enzyme and the available oxygen. Without the sensitivity provided by a thin film of conducting polymer, the change in conductivity provided by such a small conversion of analyte could go undetected.

An embodiment of a conductive sensor of the present invention is illustrated in FIG. 1, wherein a diagnostic test device 10 utilizes a conductive sensor to assay a liquid test sample for a predetermined analyte in general, and for glucose in particular. In FIG. 1a, a liquid test sample, such as a biological fluid that includes glucose, like whole blood, blood serum, blood plasma, lacrymal fluid, interstitial fluid, or urine, is introduced into the diagnostic test device 10 by a capillary tube 12. Blood is drawn by capillary action through the capillary tube 12 in the direction of the arrow in a small noninvasive amount, such as from about 0.1 μL (microliters) to about 5 μL, from a small, fresh wound. The test sample then contacts a surface of a reaction zone 14 of the conductive sensor that is in contact with capillary tube 12.

The reaction zone 14 comprises a hydratable host matrix, such as a gelatin matrix or a chitosan matrix, that is from about 0.1μ (micron) to about 10μ, and preferably from about 0.2μ to about 5μ, in thickness; and that is capable of being hydrated quickly, such as within from about 1 second to about 5 seconds, by the test sample. If the test sample is whole blood, the hydratable host matrix of reaction zone 14 preferably screens, or precipitates, the cellular material, including the red blood cells, from the serum or plasma, and fixes the cellular material in the hydratable host matrix of reaction zone 14.

In FIG. 1b, the reaction zone 14 is rapidly hydrated upon contact with the test sample. The rapid hydration of the hydratable host matrix produces a thin, continuous film 18 from about 2μ to about 10μ in thickness. The glucose concentration in the thin, continuous film 18 is essentially identical to the glucose concentration in the test sample. Therefore, an important feature of the present invention is to provide a hydratable host matrix that hydrates sufficiently fast to insure that the reaction zone 14 and the test sample have essentially the same concentration of predetermined analyte.

The chemical reagents necessary to interact with the predetermined analyte of interest and to form the dopant compound are incorporated into the hydratable host matrix of reaction zone 14. Accordingly, in the assay for glucose, the hydratable host matrix of reaction zone 14 has incorporated therein assay reagents including glucose oxidase, peroxidase or a compound capable of exhibiting peroxidase activity, and iodide ions such that the following chemical interactions (1) and (2) can occur within reaction zone 14 after the test sample contacts and quickly hydrates the substrate matrix.

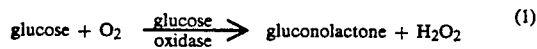

(1)

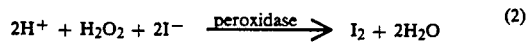

(2)

In the embodiment of the present invention illustrated in FIG. 1, in step (1) of the above interaction sequence, a portion of the glucose in the test sample interacts in reaction zone 14 with molecular oxygen ($O_2$) through the mediation of the catalyzing enzyme, glucose oxidase, to generate hydrogen peroxide. It should be understood that the hydratable host matrix includes only a limited amount of molecular oxygen. This amount of oxygen is insufficient to convert all of the glucose in the test sample to hydrogen peroxide. Therefore, in accordance with an important feature of the method of the present invention only a small amount of the glucose in the test sample is reacted, and the assay detection is performed before the amount of molecular oxygen in the hydratable host matrix is depleted.

The hydrogen peroxide ($H_2O_2$) generated in step (1), then interacts with the iodide ion ($I^-$) present in the hydratable host matrix through the mediation of the peroxidase enzyme to form molecular iodine ($I_2$) in step (2) of the chemical interaction. The molecular iodine then serves as the dopant compound. In the embodiment illustrated in FIG. 1, only a small amount of the total available glucose present in the test sample, such as less than about 1%, and as low as about 0.1%, of the total glucose present in the test sample, is converted by the enzyme interactions of steps (1) and (2) to produce molecular iodine within reaction zone 14 of test device 10. Surprisingly, the conductive sensor is sufficiently sensitive to detect the conductivity change provided by this small amount of generated molecular iodine, and the conductive sensor is so configured such that the detection measurement can be made before the oxygen concentration in the reaction zone 14 is depleted.

Therefore, in accordance with the device and method of the present invention, a sufficient amount of ambient oxygen is present in the reaction zone 14 to allow a sufficient amount of the glucose in the test sample to interact with the oxidase enzyme and generate a sufficient amount of molecular iodine to dope a layer or film of conducting polymer 16 present in a detection zone of the conductive sensor of test device 10 and cause a detectable or measurable conductivity change in the layer or film of conducting polymer 16 (FIG. 1c). Surprisingly and unexpectedly, the method and device of the present invention provide a conductive sensor that is sufficiently sensitive and operates sufficiently quickly such that low concentrations of generated molecular iodine are detected. Therefore, it is not necessary to convert the entire amount of glucose in the test sample to molecular iodine. Accordingly, the sensitivity of the conductive sensor, in addition to a configuration that allows a conductivity measurement before the oxygen supply is depleted, overcomes the oxygen limitation found in prior art methods and devices.

As previously stated, the production of molecular iodine or a similar dopant compound requires an oxygen-based chemistry. Furthermore, because of the limited amount of ambient oxygen present in the hydratable host matrix of reaction zone 14, only a small amount of the glucose present in the test sample is reacted enzymatically to eventually generate molecular iodine. The method of the present invention, therefore, is based upon a kinetic measurement of molecular iodine formation, wherein the initial rate of glucose interaction, or equivalently molecular iodine production, is measured prior to a significant depletion of the supply of ambient oxygen. The length of time prior to a significant depletion of ambient oxygen is related to the amount of glucose oxidase incorporated into reaction zone 14, the thickness of both the reaction zone 14 and the layer of conducting polymer 16 in the detection zone, the availability of ambient oxygen and the glucose concentration of the test sample. However, in considering all of these parameters, it has been found that from about ten seconds to about thirty seconds is the typical length of time before the ambient oxygen supply is significantly depleted.

The molecular iodine produced in the reaction zone 14 migrates to a detection zone of the conductive sensor that is in contact with reaction zone 14 (FIG. 1c). The detection zone includes a film or layer of conducting polymer 16 and a microelectrode assembly 20. The top surface of the film of conducting polymer 16 is in contact with the reaction zone 14, and the bottom surface of the conducting polymer 16 is in contact with the microelectrode assembly 20. In general, in the detection zone, the molecular iodine oxidatively dopes the film or layer of conducting polymer 16 and the conductivity of the film or layer of conducting polymer 16 increases. A conductometric measurement is made under a constant applied potential between two microelectrodes present in the microelectrode assembly 20 of the detection zone, and the increase, or the rate of increase, of the conductivity of the film or layer conducting polymer 16 is correlated to the glucose concentration of the test sample. To achieve the full advantage of the present invention, the rate of increase in conductivity is measured before the supply of ambient oxygen is significantly depleted, such as from within 5 seconds to 30 seconds, and preferably from within 5 seconds to 10 seconds, after the test sample contacts the reaction zone 14 of the conductive sensor of test device 10.

The sensitivity and accuracy of the device and method of the present invention are directly related to the physical and chemical properties of the components comprising the reaction zone 14 and comprising the detection zone of the test device 10. For example, in regard to the detection zone, the layer of conducting polymer 16 that is doped by the molecular iodine is included in the detection zone as a film or layer positioned in laminar contact with the microelectrode assembly 20. In particular, the microelectrode assembly 20 includes an interdigited pair of metal electrodes with an insulating spacing of from about $5\mu$ to about $300\mu$, and preferably from about $5\mu$ to about $250\mu$. To achieve the full advantage of the present invention, the interdigited pair of metal electrodes has as small an insulating spacing as possible, such as from about $5\mu$ to about $15\mu$. The microelectrode assembly 20 can be any electrode assembly capable of measuring a conductivity in the range of from about $10^{-7}$ S/cm to about $10^{-2}$ S/cm of a film or layer of conducting polymer 16 approximately 100 Å to approximately 1500 Å in thickness. Although a suitable microelectrode assembly 20 can be any one of a variety of configurations, an especially suitable configuration is illustrated in FIG. 2, and includes a pair of interdigited electrodes having gap spacings ranging from about $5\mu$ to about $15\mu$, wherein the more narrow the gap spacings, the more sensitive the conductivity measurement.

Figure 2:
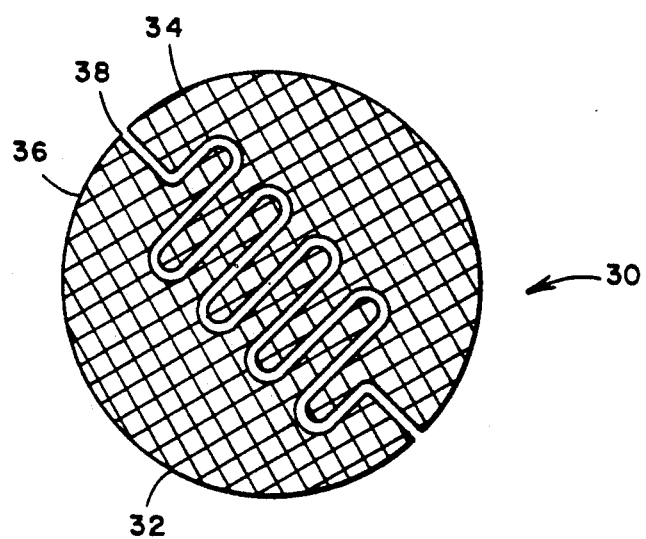
FIG. 2 is a top view of a microelectrode assembly included in the detection zone of the present invention showing the interdigited microelectrodes and the spacing, or gap, between the interdigited microelectrodes filled with the conducting polymer.

In particular, the microelectrode assembly 30 illustrated in FIG. 2 comprises a base 32 of a smooth, nonconductive material, like silicon metal, ceramic or glass. The base 32 has interdigited patterns of a conductive material 34 and 36, like a metal, applied to the top surface of the base 32. The interdigited patterns of conductive material 34 and 36 are conductively connected to conductive contacting pads (not shown) on the bottom surface of the base 32 by conductive vias (not shown) incorporated into the base 32. The interdigited patterns of conductive material 34 and 36 serve as the microelectrodes of the microelectrode assembly of the conductive sensor. Therefore, when a layer or film of conducting polymer is applied to the microelectrode assembly 30, the film or layer of conducting polymer bridges, or fills, the gap 38 between the interdigited patterns of conductive material 34 and 36 and a change in conductivity of the layer or film of conducting polymer in the gap 38 is detected by the microelectrodes comprising the interdigited patterns of conductive material 34 and 36. The manufacture of a microelectrode assembly 30 will be discussed more fully hereinafter.

In further regard to FIG. 1, in addition to the microelectrode assembly 20, another essential component in the detection zone of the conductive sensor is a thin, uniform layer or film of conducting polymer 16. The conducting polymer included in the layer or film of conducting polymer 16 usually is a heteroaromatic conducting polymer, like a polypyrrole, a poly(thienylene vinylene), a poly(furylene vinylene), a polyfuran or a polythiophene. However, a carbocyclic aromatic conducting polymer, like polyaniline, also is envisioned as useful in the method and device of the present invention. As will be discussed more fully hereinafter, a substituted polythiophene is the preferred conducting polymer because the substituted polythiophenes possess sufficient electrical properties and physical properties, like solubility in organic solvents, for a sensitive and accurate detection of the dopant compound and for easy and uniform manufacture of a thin film of conducting polymer.

Polythiophenes and polypyrroles containing long, flexible hydrocarbon chains at the 3-position of the heterocyclic rings have demonstrated solution processibility. These 3-position substituents provide processibility without significantly impairing charge transport in the doped polymers. Even with rather large substituents, the conductivities of the doped polymers can be high. As previously stated, in addition to the chemical identity of the conducting polymer, the thickness of the layer or film of conducting polymer 16 applied onto the microelectrode assembly 20 is important because the thickness of the layer or film of conducting polymer 16 is directly related to the sensitivity of the response of test device 10 to the amount of predetermined analyte in the test sample. In turn, the ability to provide a thin film of conducting polymer is directly related to the processibility of the polymer.

As the thickness of the layer or film of conducting polymer 16 decreases, the less molecular iodine is required to oxidatively dope the layer or film conducting polymer 16 to a particular conductivity value. As a result, it is desirable to have as thin a layer or film of conducting polymer 16 as possible, while retaining suitable morphological properties. Accordingly, a layer or film of conducting polymer 16 having a thickness of from about 100 Å to about 2000 Å has been found useful in the device and method of the present invention. However, a layer or film of conducting polymer 16 having a thickness of up to about 10,000 Å can be used in the method and device of the present invention, although the sensitivity of the detection of molecular iodine and the accuracy of the assay may be decreased. Preferably, the film or layer of conducting polymer 16 has a thickness of from about 100 Å to about 1500 Å. However, a lesser or a greater thickness of the layer or film of conducting polymer 16 can be utilized as long as the gap between the interdigited patterns of conductive material in the microelectrode assembly 20 is bridged, or filled, with the conducting polymer and as long as the interdigited patterns of conductive material are completely covered by the film or layer of conducting polymer 16. If the film or layer of conducting polymer 16 is too thick, a large test sample, more assay reagents and a longer assay time may be needed to achieve a sensitive and accurate assay.

The choice of conducting polymer used in the film or layer of conducting polymer 16 also is important because the conducting polymer preferably is easily processible when in solution, and exhibits rapid, facile oxidative doping upon exposure to a suitable dopant compound. A particularly useful class of polymers is the poly(3-alkylthiophene) polymers. Polyalkylthiophenes including an alkyl substituent with at least four carbon atoms exhibit significant solubility in many organic solvents including chloroform, methylene chloride, xylene and tetrahydrofuran. This solubility in organic solvents permits the use of various processing techniques that reliably and uniformly deposit thin polymer layers, or films, onto a substrate. These processing techniques include batch process techniques like spin coating, film casting, ink jet printing and similar batch process techniques. In particular, spin coating is a preferred method of depositing a layer or film of the conducting polymer onto a substrate electronic template. Similarly, polyaniline compounds can be solubilized in concentrated sulfuric acid and cast as a thin uniform film; and poly(thienylene vinylene) and poly(furylene vinylene) prepolymers are soluble and processible in the prepolymer stage and can be cast, then polymerized. Although each of these types of polymers can be processed into thin films, the processing is relatively difficult. Accordingly, polymers such as the polyalkylthiophenes that are soluble in common organic solvents for simple casting into a film are preferred. In addition, as will be demonstrated more fully hereinafter, the reagents and the hydratable host matrix comprising the reaction zone 14 can be formed into a uniform, thin layer by the same batch-type processes used to form a thin layer of conducting polymer.

In addition to suitable processing properties, the electrical properties of the poly(3-alkylthiophene) polymers, like poly(3-octylthiophene), also are suitable for use in the method and device of the present invention. Although other conducting polymers possess equal or superior electrical properties, poly(3-alkylthiophene) polymers are preferred polymers because of their suitable electrical properties and their solubility in organic solvents. For example, a thin film of a 3-alkylthiophene polymer dopes very quickly upon exposure to a dopant compound, like molecular iodine. The films of poly(3-alkylthiophene) polymers wherein the alkyl group includes from about four to about twenty carbon atoms generally are doped more quickly than films of poly(3-alkylthiophene) polymers wherein the alkyl group includes less than about four carbon atoms, such as poly(3-methylthiophene). Therefore, to achieve an optimum doping of the layer of conducting within a short time period of less than about 30 seconds, it is preferred that the alkyl chain on the poly(3-alkylthiophene) includes from about six to about twelve carbon atoms. To achieve the full advantage of the present invention, the alkyl group of the poly(3-alkylthiophene) includes from about six to about nine carbon atoms. Furthermore, a comonomer, such as thiophene, 3-methylthiophene or 3-ethylthiophene, can be included in the conducting polymer as a means of optimizing the electrical properties and the processing properties of the conducting polymer.

The morphological and electrical properties of the film or layer of conducting polymer included in the conductive sensor also can be modified by incorporating a surfactant or an inert, nonconducting polymer, such as, but not limited to, polyethylmethacrylate, polyacrylonitrile, polyethylene oxide, polyvinyldene chloride, nylon, polystyrene, polyacrylic acid, polyacrylamide, polyester, and similar nonconducting polymers, into the layer or film of conducting polymer. For example, an inert, nonconducting polymer, such as polymethylmethacrylate (PMMA), can be solubilized in an organic solvent, like chloroform, with a conducting polymer to form a casting solution. If the conducting polymer is included in the casting solution in a concentration sufficient to ensure electrical percolation, i.e. at least about 25% poly(3-octylthiophene) for a poly(3-octylthiophene)/PMMA casting solution, the final conductivity of the film of conducting polymer after oxidative doping by molecular iodine is approximately equal to the conductivity demonstrated by a doped 100% 3-alkylthiophene polymer film.

Alternatively, a copolymer of 3-octylthiophene and 3-methylthiophene can be used as the conducting polymer. The poly(3-alkylthiophene) copolymer incorporates the excellent electrical properties and affinity for molecular iodine of poly(3-methylthiophene) and the excellent solubility and processing properties of poly(3-octylthiophene) to provide a particularly useful conducting polymer. It has been found that copolymerizing a mixture including at least 90% by weight 3-octylthiophene and up to 10% by weight of 3-methylthiophene provides a copolymer that exhibits sufficient solubility for easy processing and excellent doping and electrical properties. For example, poly(3-octylthiophene) doped with ferric chloride demonstrated a conductivity of 1 S/cm, whereas, the copolymer (50:50) poly(3-octylthiophene-co-3-methylthiophene) doped with ferric chloride exhibited a conductivity of 20 S/cm. However, copolymers including such a high amount of 3-methylthiophene are not easily processed. Copolymers of various 3-alkylthiophene are described in Jen et al., U.S. Pat. No. 4,711,742.

Therefore, in general, the selection of a particular conducting polymer is limited only in that it exhibits sufficient conductivity upon oxidative doping; is sufficiently soluble in organic solvents; and is processible into a uniform layer. In general, it has been found that any conducting polymer that exhibits a solubility of at least 2 mg/ml (milligrams per milliliter) of solvent, either aqueous or organic, can be used to cast the layer of film or conducting polymer. Preferably, the conducting polymer exhibits a solubility of at least 5 mg/ml of solvent. It also is advantageous to select a conducting polymer that, when combined with a nonconducting polymer, provides a film or layer of conducting polymer that demonstrates essentially the same conductivity as a film or layer of the conducting polymer alone. Accordingly, by a judicious selection of a poly(3-alkylthiophene) and a nonconducting polymer, or by a judicious selection of a poly(3-alkylthiophene) copolymer, a film or layer of conducting polymer that is easily processed, that exhibits a high conductivity and that exhibits a favorable doping-undoping equilibrium can be provided.

In addition to the particular chemical and physical properties required of the film or layer of conducting polymer 16 and the microelectrode assembly 20 in the detection zone of the conductive sensor of the test device 10 in FIG. 1, the reaction zone 14 also should possess suitable chemical and physical properties for the device and method of the present invention to detect and accurately measure the predetermined analyte in the test sample. In general, the reaction zone 14 of the conductive sensor of test device 10 illustrated in FIG. 1 is a layer from about $0.1\mu$ to about $10\mu$, and preferably from about $0.2\mu$ to about $5\mu$, in thickness, when dry. To achieve the full advantage of the present invention, the reaction zone is a layer from about $0.2\mu$ to about $3\mu$ in thickness, when dry. However, the thickness of the layer of hydratable host matrix is limited only in that the layer is sufficiently thick to incorporate the necessary amounts of the oxidase enzyme, peroxidase and dopant compound precursor; and is sufficiently thin such that the assay can be performed within 30 seconds without interference from other compounds often found in a test sample. If the hydratable host matrix is too thick, the molecular iodine is generated relatively far from the layer of conducting polymer, therefore requiring more time for the molecular iodine to migrate to the layer of conducting polymer and providing time for the generated molecular iodine to interact with interfering compounds in the test sample, like ascorbate ion, thereby providing an inaccurate assay.

The reaction zone 14 comprises a hydratable host matrix that uniformly incorporates the oxidase enzyme, the peroxidase enzyme or a compound that exhibits peroxidase activity, like a molybdenum(VI) transition metal catalyst, and any necessary dopant compound precursors, like iodide ion. A suitable hydratable host matrix includes materials such as gelatin, silk fibroins, chitosan, collagen, and polyacrylamide; or combinations thereof. The preferred hydratable host matrix is gelatin, chitosan or silk fibroins, or a combination thereof. To achieve the full advantage of the present invention, gelatin or chitosan is included in the hydratable host matrix.

In accordance with an important feature of the present invention, the dry, hydratable host matrix is capable of rapid hydration upon contact with the liquid test sample, such as within about 5 seconds. In particular, the method of the present invention utilizes an early conductivity measurement, i.e. within about 30 seconds, and preferably within about 10 seconds, after the test sample contacts the reaction zone 14, to determine the rate of molecular iodine formation, or equivalently, the rate of glucose conversion. Therefore, it is important that the dry, hydratable host matrix hydrates before a substantial interaction between the predetermined analyte and the oxidase enzyme occurs. It also is important that the diffusion rates of all interactants and interaction products, like molecular iodine, through the hydratable host matrix are sufficiently high such that the interactions can proceed quickly, and that the generated molecular iodine can quickly and effectively migrate to the detection zone of conductive sensor to dope the layer or film of conducting polymer film 16.

In addition, because the oxidase enzyme is not present in the reaction zone 14 in an excess amount, it also is important that the oxidase enzyme remains stable within the hydratable host matrix over potentially long storage periods. Finally, the processing technique used to apply the reaction zone 14 to the conductive sensor must not disrupt the integrity of the film or layer of conducting layer 16 present in the underlying detection zone. It also is envisioned that the oxidase enzyme, peroxidase enzyme and iodide ion, or other dopant compound precursor, can be isolated from one another within the dry hydratable host matrix, as long as these components diffuse sufficiently rapidly such that the host matrix is homogeneous when it is hydrated by the liquid test sample.

The method of the present invention, used to assay a test sample for a predetermined analyte capable of undergoing an interaction with an oxidase enzyme, is both new in the art and is distinct from the other known electrochemical sensors for such analytes. For example, the commercial prior art sensors include amperometric glucose probes and other investigators are attempting to miniaturize potentiometric glucose probes. In addition to differing from the prior art devices and methods, the present invention demonstrates advantages that help overcome the major problems and disadvantages common to most, if not all, of the prior art electrochemical glucose and related sensors.

For example, a major problem in electrochemical glucose and related sensors is the need for a sufficient amount of oxygen to interact with the entire amount of analyte present in the test sample. Originally, the oxygen limitation problem was overcome by diluting the blood or serum sample. Although, early electrochemical sensors depended upon dilution to eliminate oxygen limitations, dilution limited the applicability of electrochemical sensors in decentralized test markets. Accordingly, to eliminate oxygen limitations and avoid test sample dilutions, investigators began incorporating a mediator other than oxygen for the electron transfer reactions of glucose oxidase. Such oxygen substitutes include 1,1′-dimethylferrocene and ferricinium ion mediators. Other investigators relied upon direct electron relays between the oxidase enzyme and the electrode surface.

However, the device and method of the present invention eliminate the problem of oxygen limitation more easily and provide fast assays performed on small, undiluted test samples. In the embodiment illustrated in FIG. 1, the improved sensitivity of the device and method results from a technique that utilizes a kinetic measurement of the rate the initial analyte-oxidase interaction before an appreciable amount of the ambient oxygen supply, or an appreciable amount of the analyte in the test sample, has been consumed in the interaction. In general, only from about 0.1% to about 1% of the available predetermined analyte in the test sample has been consumed at the time the conductometric measurement is made. Therefore, the oxygen limitation problem is overcome. Accordingly, the device and method of the present invention do not require oxygen-substitute mediators or additional manipulative steps, like dilution. In addition, the analyte assay is fast, simple, sensitive and accurate.

Accordingly, the method of the present invention comprises introducing a test sample, such as from about 0.1 $\mu$L to about 5 $\mu$L, and usually less than 1 $\mu$L, of a whole blood sample, into the capillary tube 12 of test device 10 illustrated in FIG. 1; then determining the change of conductivity in the layer of conducting polymer 16 in the detection layer within a time period of from about 5 sec. to about 30 sec. after the test sample contacts the reaction zone 14 of the conductive sensor of the test device 10. The change in conductivity of the layer or film of conducting polymer 16 is measured by the microelectrode assembly 20 and can be correlated to the amount of predetermined analyte in the test sample by comparison to the change in conductivity of a layer or film of conducting polymer 16 exhibited by standardized solutions of the predetermined analyte. Accordingly, a fast, simple, sensitive and accurate assay for glucose, or other analytes capable of interacting with an oxidase enzyme, is provided.

Figure 3:
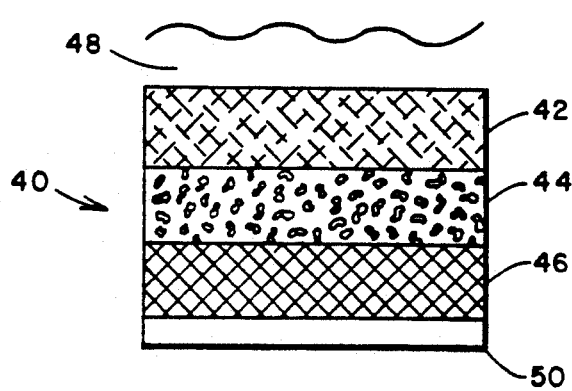
FIG. 3 is a partial side view in cross-section of a preferred embodiment of the conductive sensor of the present invention.

The preferred embodiment of the present invention is illustrated in FIG. 3, wherein a conductive sensor 40 is utilized to assay for a predetermined analyte, such as glucose, in a test sample 48. The conductive sensor 40, like the conductive sensor in the test device 10 illustrated in FIG. 1, includes a reaction zone 44 in laminar contact with a detection zone including a film or layer of a conducting polymer 46 and a microelectrode assembly 50 that are essentially identical to the reaction zone 14 and the detection zone of the conductive sensor of test device 10 of FIG. 1 described above. For example, reaction zone 44 includes the necessary oxidase enzyme to interact with the predetermined analyte of interest, peroxidase and a dopant compound precursor, if necessary, to generate a dopant compound. However, unlike the conductive sensor of test device 10 in FIG. 1, the reaction zone 44 of conductive sensor 40 includes an excess amount of oxidase enzyme and peroxidase to convert a sufficient amount of the predetermined analyte in the test sample 48 to the dopant compound. In addition, the detection zone includes a layer or a film of conducting polymer 46 that is oxidatively doped by the dopant compound generated in reaction zone 44 and that migrates into detection zone.

However, whereas the test device 10 of FIG. 1 relied upon measuring the initial rate of interaction between the predetermined analyte and the oxidase enzyme included in reaction zone 14, the conductive sensor 40 illustrated in FIG. 3 controls the amount of the dopant compound that migrates into the detection zone from reaction zone 44 by limiting the migration of the test sample 48 into the reaction zone 44 by a semipermeable membrane 42. By limiting the amount of the test sample 48, and therefore glucose, migrating through the restrictive semipermeable membrane 42 to reaction zone 44, and by interacting and converting substantially all of the glucose migrating into reaction zone 44 to generate a dopant compound, the amount of glucose in the test sample 48 is determined by correlating the rate of change in conductivity of the layer or film of conducting polymer 46 in the detection zone to the diffusion rates of the test sample 48 through the semipermeable membrane 42.

In particular, the test sample 48 including the predetermined analyte contacts the semipermeable membrane 42, and the test sample 48 permeates through the semipermeable membrane 42 at a relatively slow, uniform rate. The permeation rate is a function of the analyte concentration of interest in the test sample 48. In effect, the migration of the test sample 48 through the semipermeable membrane 42 is the rate limiting step of the interaction. When the test sample 48 contacts the reaction zone 44, an interaction between the predetermined analyte, like glucose, and the oxidase enzyme, like glucose oxidase, generates, either directly or indirectly, a dopant compound, like molecular iodine. In this particular embodiment, and in contrast to the embodiment illustrated in FIG. 1, a sufficient amount of the oxidase and peroxidase enzymes are incorporated into the reaction zone 44 to insure that the permeation rate of glucose is the dominant limitation.

The dopant compound, like molecular iodine generated in the reaction zone 44, then migrates to the detection layer to oxidatively dope the layer or film of conducting polymer 46 present in the detection zone of the conductive sensor 40. Accordingly, the layer or film of conducting polymer 46 exhibits an increase in conductivity, with the increase in conductivity being related to the migration rate of the predetermined analyte through semipermeable membrane 42. The increase in conductivity is detected by a microelectrode assembly 50 that is in contact with the layer or film of conducting polymer 46. Therefore, the concentration of the predetermined analyte is determined indirectly from the migration rate of the predetermined analyte in the test sample 48 through the semipermeable membrane 42.

An important feature of the preferred embodiment depicted in FIG. 3 is the semipermeable membrane 42. The semipermeable membrane 42 has physical and chemical properties that allow the relatively slow, but uniform, migration of the predetermined analyte to the reaction zone 44. Furthermore, the permeation rate of ambient oxygen into, and through, the semipermeable membrane 42 is sufficiently high such that an oxygen limitation on the enzymatic interactions occurring within the reagent zone 44 is precluded. In particular, the semipermeable membrane 42 generally exhibits a diffusion constant for molecular oxygen of from about $5 \times 10^{-7}$ cm$^2$/sec to about $5 \times 10^{-6}$ cm$^2$/sec, and for species such as glucose ranging from about $1 \times 10^{-9}$ cm$^2$/sec to about $5 \times 8^{-8}$ cm$^2$/sec. Preferably, the semipermeable membrane 42 is compatible with biological fluids, like blood and urine, and, to achieve the full advantage of the present invention, selectively screens assay interferents, like ascorbate and uric acid, from the test sample 48. Silicone-containing elastomers, applied as a film with a thickness of from about $3\mu$ to about $15\mu$, and preferably from about $5\mu$ to about $10\mu$, are useful as the semipermeable membrane 42. Other suitable semipermeable membranes include porous polypropylene, porous nylon, porous polycarbonate, porous polyurethane, and similar porous materials; and combinations thereof. To achieve the full advantage of the present invention, the semipermeable membrane 42 is a film of from about $6\mu$ to about $8\mu$ in thickness.

In the preferred embodiment illustrated in FIG. 3, the semipermeable membrane 42 retards the available glucose in the test sample 48 from rapid contact with the reaction zone 44. It also should be understood that although ambient oxygen can permeate through the semipermeable membrane 42 that the permeation is not sufficient to provide sufficient oxygen to interact with all the available glucose in the test sample 48. Therefore, the semipermeable membrane 42 retards the migration of the available glucose to the reaction zone 44 such that only about 3% or less of the available glucose reaches the reaction zone 44. Accordingly, the reaction zone 44 includes a sufficient amount of oxidase enzyme, peroxidase enzyme and ambient oxygen to interact with the glucose that does migrate to the reaction zone 44. This interaction is detected quickly, such as within 30 seconds, and preferably within 10 seconds, before continuing amounts of glucose migrate to the reaction zone 44 and encounter an oxygen limitation problem due to insufficient permeation of ambient oxygen to the reaction zone 44.

Therefore, the semipermeable membrane 42 has a sufficient thickness, like from about $3\mu$ to about $15\mu$, to retard the migration of glucose to the reaction zone 44. As the thickness of the semipermeable membrane 42 increases, like above about $15\mu$, the time required to perform the assay is increased. Therefore, a thin semipermeable membrane 42 is preferred.

Therefore, the semipermeable membrane 42 preferably is a relatively thin film, of from about $6\mu$ to about $8\mu$, that is permeable to both ambient oxygen and the predetermined analyte. A semipermeable membrane 42 demonstrating a diffusion constant for oxygen of from about $5 \times 10^{-7}$ cm$^2$/sec to about $5 \times 10^{-6}$ cm$^2$/sec allows sufficient oxygen to enter the reaction zone 44 such that oxygen limitations are avoided. Furthermore, the semipermeable membrane 42 also should demonstrate a diffusion constant for the predetermined analyte, like glucose, of from about $1 \times 10^{-9}$ cm$^2$/sec to about $5 \times 10^{-8}$ cm$^2$/sec. A semipermeable membrane 42 exhibiting this diffusion rate sufficiently retards the major amount of the predetermined analyte in test sample 48 from contacting the reaction zone 44, but permits a sufficient and known minor amount of the predetermined analyte to contact the reaction zone 44 for a rapid and accurate analyte determination. It is preferred that the semipermeable membrane 42 be as thin as possible to allow migration of the predetermined analyte and to eliminate interfering compounds. Accordingly, to provide a thin semipermeable membrane, the diffusion constant the predetermined analyte through the semipermeable membrane should be sufficient to allow an assay to be performed within 30 seconds, and preferably within 10 seconds.

The semipermeable membrane 42 also provides the advantage of eliminating the effects of interfering compounds present in the test sample. As noted above, the generated molecular iodine can interact with common test sample components, such as ascorbate, uric acid, acetaminophen, and salicylates, before the molecular iodine can dope the conducting polymer. This problem is partially resolved by utilizing a thin reaction zone 44 to generate the molecular iodine near the conducting polymer such that doping of the conducting polymer occurs before the oxidation of interfering compounds. The semipermeable membrane 42 further resolves this problem by selectively screening anionic interfering compounds from the test sample 48. The anionic interfering compounds demonstrate a diffusion constant of only about $1 \times 10^{-11}$ cm$^2$/sec to about $1 \times 10^{-10}$ cm$^2$/sec through the semipermeable membrane 42. Therefore, because the diffusion rate of the interfering compound through the semipermeable membrane 42 is much slower than the diffusion rate of the predetermined analyte, the assay has been completed before an appreciable amount of the interfering compounds migrate to the reaction zone 44. Furthermore, the semipermeable membrane 42 effectively screens cellular material from the test sample 48, like the red blood cells in a whole blood sample, without clogging and further retarding the diffusion of the predetermined analyte through the semipermeable membrane 42. Therefore, low molecular weight components in the blood plasma or blood serum can migrate to the interaction layer 44.

In comparison to test device 10 of FIG. 1, the conductive sensor 40 of FIG. 3 provides as fast an assay and substantially reduces the effects of interfering compounds often found in the test sample. For example, if the semipermeable membrane 42 is a silicone-containing elastomer of approximately 6$\mu$ in thickness, the assay for the predetermined analyte in the test sample 48 still can be completed within about 30 seconds, and usually within about 10 seconds. As will be demonstrated more fully hereinafter, the semipermeable membrane 42 can be applied, reproducibly, as a thin, uniform layer, such that from the thickness of the semipermeable membrane and the diffusion constant of the predetermined analyte through the semipermeable membrane, the amount of predetermined analyte that contacts the reaction zone 44 for interaction with the enzymes and generation of molecular iodine can be detected and measured. This measurement then can be correlated to the total amount of available predetermined analyte in the test sample.

To demonstrate the accuracy and sensitivity of a conductive sensor and the method of the present invention, the following test device was prepared and used in an assay for glucose. The test device included a conductive sensor 40 illustrated in FIG. 2. First, the microelectrode assembly 50 of FIG. 3, and more fully illustrated as the microelectrode assembly 30 in FIG. 2, was prepared. Accordingly, a wafer or layer of a smooth, nonconductive material, for example, but not limited to, silicon, ceramic, teflon, polycarbonate, polypropylene, kevlar, chrome-treated glass and glass, was used as the base 32 of the microelectrode assembly 30 in FIG. 2 for the subsequent deposition of the interdigited patterns of conductive material 34 and 36.

Interdigited patterns of conductive material 34 and 36 are applied to the top surface of base 32, and conductive contacting pads (not shown) for electrical connection to detection instrumentation are applied to the bottom surface of base 32. The conductive contacting pads and the interdigited patterns of conductive material 34 and 36 are usually a metal, and preferably are gold. Other suitable materials include silver, cermet, nickel and platinum In general, the only limitation on the material used as the conductive pads and the interdigited patterns of conductive material 34 and 36 is that an ohmic contact exists between the material and the layer or film of conducting polymer. Accordingly, aluminum is not a suitable material. The top and bottom surface conductors, i.e. the interdigited patterns of conductive material 34 and 36 and the conductive contacting pads respectively, are connected by vias through the base 32. The interdigited patterns of conductive material 34 and 36 on the top surface of base 32 have a finger-like appearance and have about a 10$\mu$ and about a 10$\mu$ gap and finger widths, respectively. In general, the gap widths range from about 10$\mu$ to about 300$\mu$, and the finger widths range from about 10$\mu$ to about 300$\mu$. Finger lengths range from about 100$\mu$ to about 400$\mu$ and usually are from about 150$\mu$ to about 350$\mu$. The total channel length ranges from about 100$\mu$ to about 400$\mu$ and usually is from about 150$\mu$ to about 350$\mu$.

Therefore, a test device of the present invention utilizes a smooth and nonconductive base for the microelectrode assembly, wherein the top, or sensing, surface of the microelectrode assembly includes an interdigited metal pattern, like a gold pattern, printed onto the base of the microelectrode assembly by procedures well known in the art. Electrical contact to the top sensing surface of the microelectrode assembly is accomplished by gold vias to the back surface of the base of the microelectrode assembly. Large gold contact pads positioned on the back surface of the base of the microelectrode assembly provide an electrical connection to detection instruments, such as a conductivity meter. This particular configuration isolates the top, sensing surface of the microelectrode assembly from the contact pads on the bottom surface of the base of the microelectrode assembly, and therefore avoids making an electrical contact to detection instruments through the chemical layers of the reaction zone and detection zone that subsequently are positioned over the top sensing surface of the microelectrode assembly.

More particularly, on the top sensing surface of the electrode assembly two isolated halves of deposited metal on the surface form an interdigited pattern. The overall dimensions of this interdigited pattern ranged from 0.9 cm in diameter for gold printed on circular ceramic to 687$\mu$ by 850$\mu$ for gold patterned on rectangular silicon. The number of fingers protruding from each half was four and twenty respectively. This undulating channel between each isolated half is generally 250$\mu$ wide and 33 mm long for the ceramic devices and 10$\mu$ wide and 27 mm long for the silicon devices. Finger widths are 250$\mu$ and 10$\mu$ for the ceramic and silicon devices, respectively. The fingers generally extend about 300$\mu$ and are about 10$\mu$ wide. In accordance with an important feature of the present invention, the test device measures the conduction of electrons from one half of the isolated interdigited pattern to the other half of the pattern. Therefore, the size of the gap between each isolated half of the interdigited pattern is an important feature of the test device because the analyte assay is more sensitive and more accurate as the gap is reduced.

Accordingly, after manufacturing a microelectrode assembly, a layer or film of conducting polymer, from about 100 Å to about 10,000 Å in thickness, is deposited in the gap between the isolated interdigited patterns of conductive material. Then a reaction zone, from about $0.1\mu$ to about $10\mu$ in thickness, is deposited over the layer of conducting polymer, such that a dopant compound is produced upon contact between the reaction zone and a test sample, and dopes the conducting polymer. Above the reaction zone is deposited a semipermeable membrane of about $3\mu$ to about $15\mu$ in thickness.

Therefore, onto the top sensing surface of the microelectrode assembly is positioned a layer or film of a suitable conducting polymer. As stated previously, a suitable conducting polymer provides a resistance upon exposure to molecular iodine in the range from about $10^1$ ohm to about $10^9$ ohm when the polymer film has a thickness of from about 100 Å to 1000 Å. Furthermore, the conducting polymer should be stable and easy to process such that the conducting polymer can be applied to the microelectrode assembly as a uniform, thin film or layer by spin coating, film casting, jet printing or a similar application technique known in the art. The thickness of the film or layer of the conducting polymer is sufficient to fill the gaps between the two isolated interdigited patterns on the substrate electronic template and to completely coat, or cover, the interdigited patterns such that the interdigited patterns of conducting material do not contact the reaction zone of the conductive sensor.

Accordingly, suitable conducting polymers include, but are not limited to, the polythiophenes, polypyrroles, polyfurans, poly(thienylene vinylenes), and poly(furylene vinylenes) that demonstrate sufficient solubility in organic solvents to be processed into a film. Preferably, the conducting polymer is a polythiophene, such as a poly(3-alkylthiophene), wherein the alkyl group includes from about four to about twenty, and preferably from about six to about twelve, carbon atoms. To achieve the full advantage of the present invention, the alkyl group of the poly(3-alkylthiophene) includes from about six to about nine carbon atoms. These particular polythiophenes have demonstrated a sufficient electrical conductivity and satisfactory processing properties, such as solubility in organic solvents, to provide a thin, uniform layer or film of conducting polymer on the microelectrode assembly. As previously discussed, the conducting polymer can be admixed with nonconducting polymers, or the conducting polymer can be a copolymer, to improve the processing, physical and morphological properties of the film or layer of the conducting polymer.

Therefore, in the manufacture of a conductive sensor 40 of FIG. 3, a particularly useful conducting polymer, poly(3-octylthiophene), first was dissolved in a suitable solvent, like xylene, at a concentration of 5 mg (milligrams) of conducting polymer per ml (milliliter) of solvent. In general, it has been found that the concentration of the conducting polymer in the solvent should range from about 2 mg/ml to about 15 mg/ml, and preferably from about 3 mg/ml to about 10 mg/ml. More concentrated solutions of the conducting polymer also can be used as long as the viscosity of the solution is suitable for casting a uniform, thin film of conducting polymer.

Other suitable solvents that can be used in place of, or in addition to, xylene include, but are not limited to, benzene, toluene, chloroform, methylene chloride, trichloroethylene, tetrahydrofuran, 1,2-dichloroethane, nitrobenzene, dimethylsulfoxide, dimethylformamide; and combinations thereof. In general, any organic solvent capable of solubilizing the conducting polymer and having a sufficient vapor pressure to evaporate from the film of conducting polymer is suitable for use in the present invention.

Before applying the solution of the conducting polymer to the microelectrode assembly, the microelectrode assembly is cleaned with a solvent, like chloroform, by washing the microelectrode assembly, then spinning the electronic template dry on a PHOTO-RESIST SPINNER, available from Headway Research Inc., Garland, Tex. With the microelectrode assembly at rest on the spinner, the top sensing surface of the microelectrode assembly is flooded with the conducting polymer-xylene solution and then spun to dryness at 3000 rpm for approximately 20 seconds on the PHOTO-RESIST SPINNER to produce a thin, uniform film. The conducting polymer film then is allowed to air dry for at least 30 minutes. The dried layer, or film, of conducting polymer has a thickness of approximately 200 Å to approximately 300 Å.

After the layer or film of conducting polymer has dried sufficiently, the reaction zone is positioned in laminar contact with the top surface of the layer or film conducting polymer. The reaction zone comprises the hydratable host matrix homogeneously incorporating a suitable oxidase enzyme and other enzymes and dopant compound precursors to interact with the predetermined analyte and to generate a dopant compound. The reaction zone is sufficiently thick such that a sufficient amount of enzymes and dopant compound precursors can be included in the reaction zone, and is sufficiently thin such that the dopant compound is generated near the layer or film of conducting polymer to dope the conducting polymer before the dopant compound undergoes an interaction with an interfering compound present in the test sample.

Accordingly, in the preparation and application of the reaction zone to the test device, the following stock gelatin solution (20% W/W) was prepared by adding about 140 g (grams) of gelatin, such as GELATIN ZKN-407, available from Sigma Chemical Co., St. Louis, Mo., in 560 g of distilled water. After allowing the gelatin to swell in the water approximately 15 to approximately 20 minutes, the gelatin-water mixture was heated to about 45° C. to melt the gelatin. After approximately one to 3 hours, the gelatin was melted and the pH of the gelatin-water mixture was adjusted to 7.0 with sodium hydroxide. The stock gelatin solution then was stored at a temperature of from 0° C. to 5° C. In this particular embodiment, gelatin was used as the hydratable host matrix of the reaction zone. However, other suitable materials useful as the hydratable host matrix include, but are not limited to, collagen, silk fibroin, crosslinked albumin, a polyacrylamide and poly(2-hydroxyethylmethacrylate) and combinations thereof.

After forming the stock gelatin solution, a gelatin casting composition was prepared. This particular casting composition included:

| | | |
|---|---|---|
| Gelatin (20% W/W) | 50.00% | (by weight) |
| BES buffer 1M, pH 7 | 5.00% | |
| GOD | 0.11% | |
| POD | 0.44% | |
| Distilled Water | 44.45% | |
| | 100.00%, | | wherein the gelatin is the stock gelatin solution described above; BES is a buffer solution including N,N-bis(2-hydroxyethyl)-2-aminoethane sulfonic acid and sodium N,N-bis(2-hydroxyethyl)-2-aminoethane sulfonate; GOD is glucose oxidase having an activity of at least about 85 U/mg (units per milligram, wherein a unit is defined as the ability to oxidize 1.0 μmole (micromole) of β-D-glucose to D-gluconic acid and hydrogen peroxide per minute at pH 5.1 at 35° C.); and POD is a peroxidase enzyme having an activity of approximately 1160 U/mg (units per milligram, wherein a unit is defined as the ability to form one mg purpurogallin in 20 seconds from pyrogallol at pH 6.0 and 20° C.) and an RZ of at least 3, wherein the term RZ is a measure of hemin content and can be indicative of enzyme purity. Suitable peroxidase enzymes include, but are not limited to, horseradish peroxidase, lactoperoxidase, microperoxidase or combinations thereof. However, it should be understood that other compounds that have peroxidase activity, i.e. behave like peroxidase in the presence of hydrogen peroxide, also can be included in the hydratable host matrix in addition to or in place of the peroxidase. Compounds exhibiting peroxidase activity that can be included in the hydratable host matrix include, but are not limited to, molybdenum(VI) transition metal catalysts and similar transition metal catalysts. Molybdenum(VI) transition metal catalysts are known to interact with hydrogen peroxide to convert iodide ion to molecular iodine. Furthermore, other suitable buffers well-known in the art, such as phosphate buffers, also can be used in the casting solution.

It should be understood that the above gelatin casting composition was used when glucose was the predetermined analyte of interest However, if a different analyte is of interest, the GOD is replaced by the appropriate oxidase enzyme that interacts with that particular predetermined analyte. For example, if alcohol is the predetermined analyte of interest, a sufficient amount of alcohol oxidase replaces the GOD.

The gelatin casting composition was prepared by melting 50 g of the 20% stock gelatin solution in a 45° C. water bath. In a separate beaker, the buffer and distilled water were premixed to form an aqueous buffer solution. The GOD and POD then were added to the aqueous buffer solution. After the enzymes were dissolved in the aqueous buffer solution, and after the stock gelatin solution was melted, the two solutions were combined and the resulting mixture was stirred gently at 40°–45° C. for at least 15 minutes.

The above-described gelatin casting composition illustrates a casting composition that provides a reagent zone of a conductive sensor of the present invention. In general, it has been found that a suitable casting composition comprises:

| | |
|---|---|
| Hydratable host matrix | 2% to 20% (dry basis) (by weight) |
| Buffer | q.s. to sufficiently buffer to about pH 7[1] |
| Oxidase Enzyme | 0.05% to 1.5% |
| Peroxidase Enzyme | 0.4% to 0.6% |
| Dopant Compound Precursor | 0% to 2% |
| Water | q.s. to 100% |

[1]For example, 1M BES buffer, 4% to 6% by weight provide pH 7.

1) For example, 1 M BES buffer, 4% to 6% by weight to provide pH 7.

In addition to preparing the casting composition, a crosslinking composition including the following ingredients was prepared by simply admixing the composition ingredients, and stirring, to provide a homogeneous crosslinking composition. The composition pH then was adjusted to about 7.

| | |
|---|---|
| EDAC | 2.0% (by weight) |
| SURFACTANT 10 G (5% aqueous solution) | 8.0% |
| BES buffer 1M, pH 7 | 2.5% |
| Distilled Water | 87.5% |
| | 100.0% |

In the above crosslinking composition, EDAC is 1-ethyl-3-(3-dimethylaminopropyl)carbodiimide, available from Sigma Chemical Co., St. Louis, Mo., and used to harden and crosslink the gelatin-based hydratable host matrix of the reaction zone. Other suitable crosslinking agents include, but are not limited to, the crosslinking reagents listed in the 1987 catalog of Sigma Chemical Co., St. Louis, Mo., on page 452. SURFACTANT 10G is a nonylphenol-polyglycidol surfactant, available from Olin Chemical, Stamford, Conn. This optional surfactant ingredient is included to improve the overall coating properties of the gelatin-based film. In general, a suitable crosslinking composition comprises from about 1% to about 5%, and preferably from about 2% to about 3%, by weight of a crosslinking agent; from 0% to about 1%, and preferably from about 0.3% to about 0.4%, by weight of a surfactant; a sufficient amount of a buffer to maintain a pH of about 7; and water.

The reaction zone was incorporated onto the test device by first applying the casting composition and then the crosslinking composition to the test device with a PHOTO-RESIST SPINNER. The PHOTO-RESIST SPINNER, or an equivalent device, reproducibly applies a thin, uniform reaction zone film. First, an aliquot of the gelatin casting solution was applied over the layer or film of conducting polymer. The spinner was rapidly accelerated to approximately 2000 rpm, and maintained at approximately 2000 rpm for approximately 20 seconds. The resulting wet film of gelatin casting solution was allowed to air dry for approximately 15 minutes, and the film of gelatin casting composition had hardened sufficiently to allow application of the crosslinking composition. The crosslinking composition then was applied over the entire wet gelatin film surface. After a short contact time between the crosslinking composition and the wet film of gelatin casting composition, the test device again was spun on the PHOTO-RESIST SPINNER. Then, the test device was allowed to air dry for at least about 1 hour before use. The dried, crosslinked gelatin-based reaction zone film had a thickness of from approximately 1μ to approximately 3μ.

Then, positioned in laminar contact with the top surface of the reaction zone, a thin film of a silicone elastomer was applied to the conductive sensor. The silicone elastomer served as the semipermeable membrane. The semipermeable membrane was applied to the conductive sensor by the same batch type processes described above to provide, reproducibly, a thin, uniform film of silicone elastomer having a thickness of about 6μ to about 8μ. It should be understood that for each of the three layers or films, i.e. the conducting polymer, the reaction zone and the semipermeable membrane, once the desired thickness of the film is determined, the semiconductor processing techniques utilized to manufacture the conductive sensors provide layers or films that are reproducible to within ±5% in thickness. It is important that the thickness of each layer be controlled such that the thickness of the individual layers is essentially eliminated as a variable parameter in the assay for a predetermined analyte. Therefore, in accordance with an important feature of the present invention, the thickness of each layer is controlled to within ±5% of the desired, predetermined thickness.

The ability to reproducibly provide thin films of uniform thickness is an important feature of the present invention. For example, the ability to provide uniform, thin films allows the economical and facile manufacture of miniaturized test devices. Therefore, extremely small test samples can be used, such as from about 0.1 μL to about 5 μL. In contrast, present test devices require at least about 5 μL, and up to about 20 μL of test sample to provide an accurate assay. These larger-sized blood samples require invasive and more painful test sample acquisition techniques. The miniature size of the test device also allows the economical manufacture of a disposable test device.

In addition to allowing the easy and economical manufacture of disposable test devices that require very small sample sizes, the ability to reproducibly cast uniform thin films provides a fast and accurate assay for a predetermined analyte. The thin films allow a sufficient amount of the predetermined analyte to migrate through the semipermeable membrane to contact the reaction zone and interact with the enzymes and the dopant compound precursor. After interacting to generate the dopant compound, the conducting polymer then is doped to provide an assay within about 30 seconds, and preferably within about 10 seconds. In addition, the assay is accurate and sensitive because the films or layers are sufficiently thin such that the dopant compound is generated in proximity to the conducting polymer layer. Accordingly, the dopant compound can dope the conducting polymer before undergoing reactions with interferent compounds often present in the test sample. Therefore, essentially all the dopant compound is available to dope the polymer to provide an accurate assay. Furthermore, because the conducting polymer is thin, the sensitivity of the conductive sensor is increased because a relatively large change in conductivity is observed for a relatively small amount of generated dopant compound.

The ability to reproducibly provide thin uniform films also is important because only a small portion of the total available predetermined analyte in the test sample is interacted to generate the dopant compound. Therefore, to accurately correlate the change in conductivity of the conducting polymer to the total amount of predetermined analyte in the test sample, the layers in the conductive sensor are manufactured at a reproducible thickness such that assay measurements are indicative of the actual concentration of predetermined analyte in the test sample, and not of the apparent concentration of predetermined analyte in the test sample because of appreciable thickness variances in any of the three films or layers in the sensor.

In accordance with an important feature of the present invention, a test device prepared by the above described method, but lacking the semipermeable membrane, i.e. a test device 10 of FIG. 1, accurately assayed standardized glucose solutions including from 25 mg/dL to 500 mg/dL glucose. The standardized glucose solutions further included iodide ions. As discussed above, in a test device of the present invention however, the iodide ions are included in the reaction zone of the conductive sensor in an amount ranging from about 30 mM to about 500 mM. The conductivity of the film or layer of conducting polymer in the detection zone was measured at an applied voltage of 0.1 V (volt), and electrical currents the range of from 0.1 μamp (microamp) to 5 μamp were found as typical.

Figure 4:
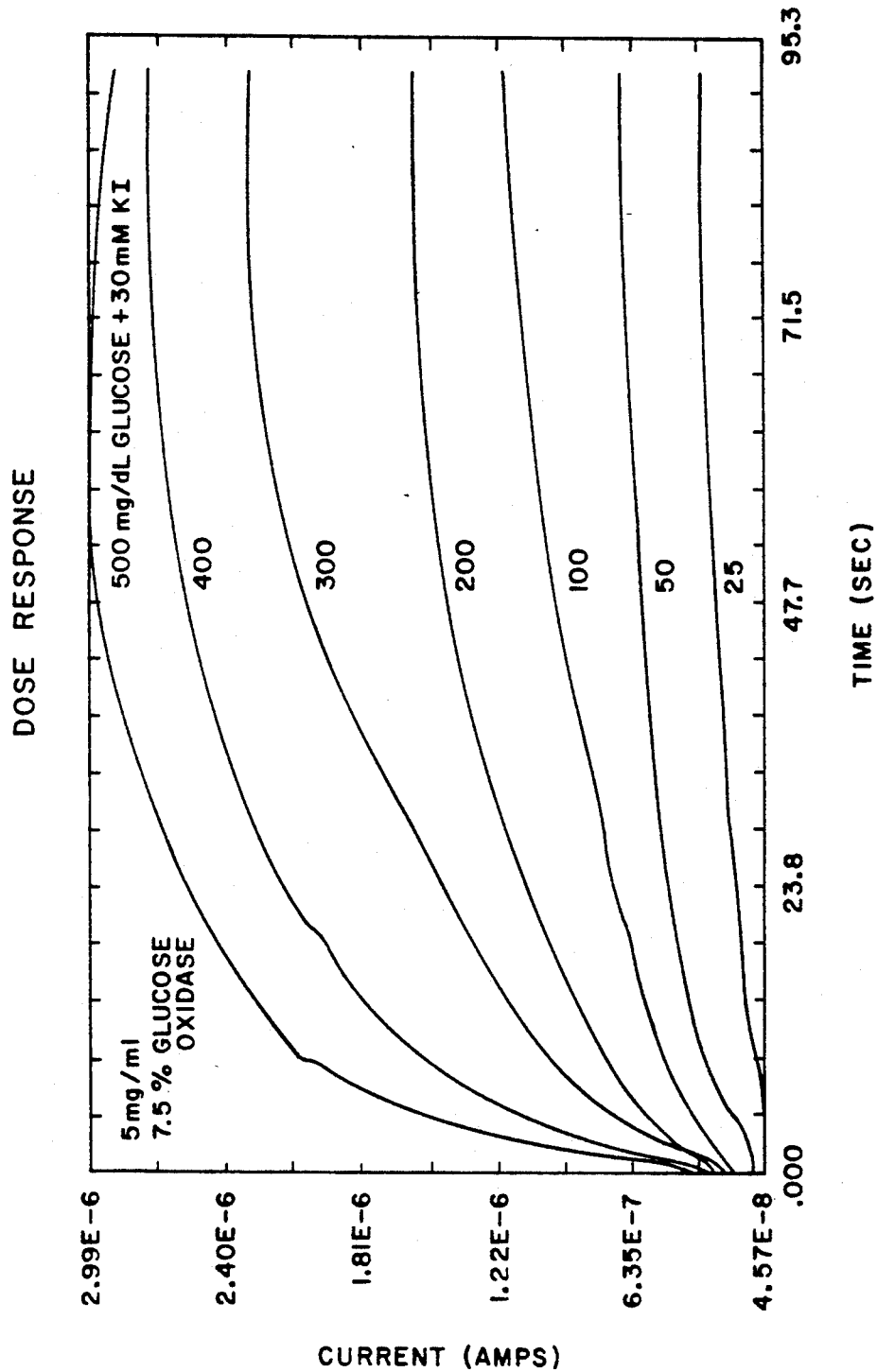
FIG. 4 is a dose response plot of current (amps) vs. time (seconds) for assays of standardized solutions including 30 mM (millimolar) potassium iodide and either 25, 50, 100, 200, 300, 400 or 500 mg/dL (milligrams per deciliter) of glucose assayed by the method and conductive sensor of the present invention.
Figure 5:
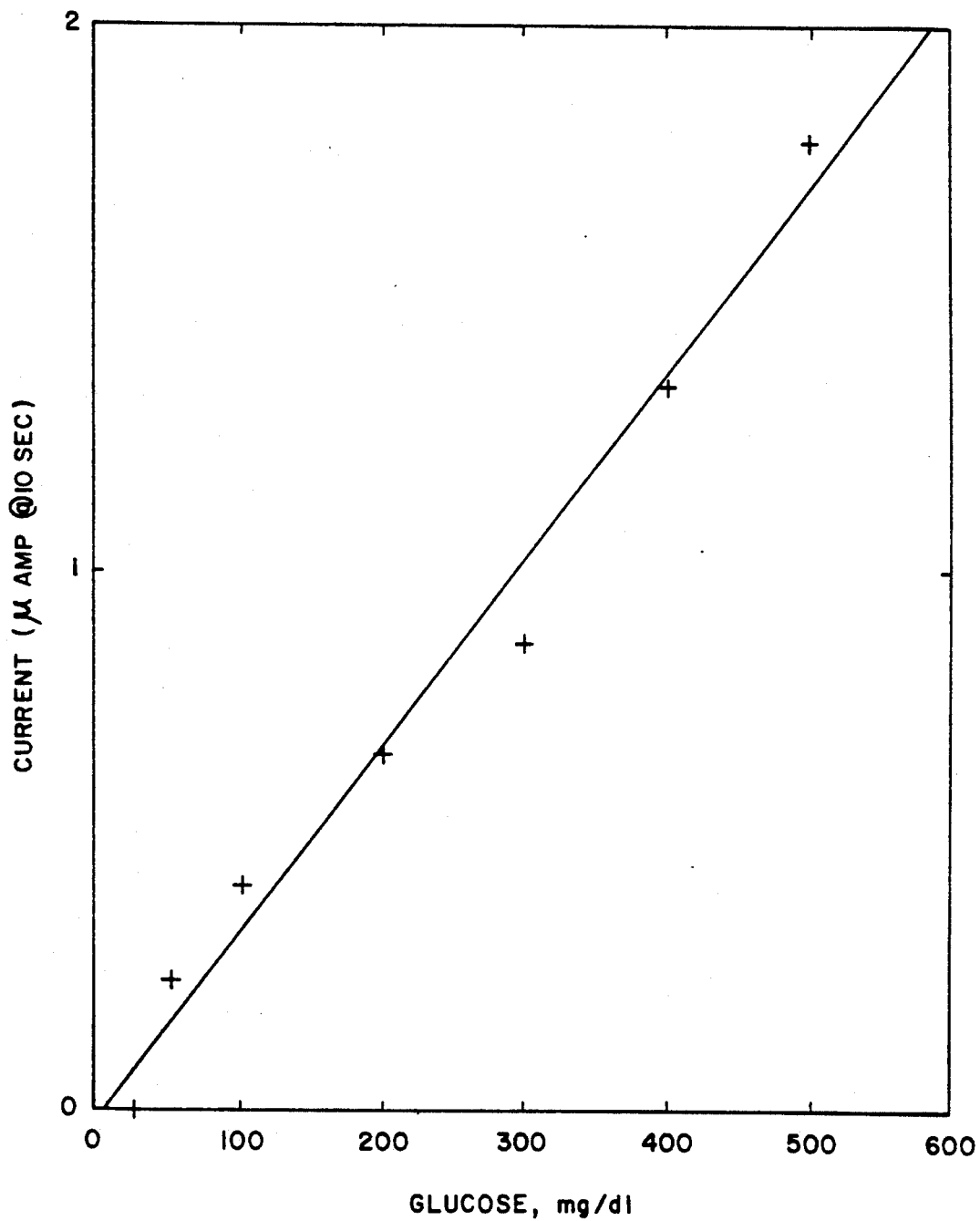
FIG. 5 is a plot of current (microamps at 10 sec.) vs. glucose concentration (mg/dL) showing the linear relationship between the concentration of glucose in a standardized test sample and conductivity of the layer of conducting polymer exhibited by a conductive sensor of the present invention.

As will be demonstrated more fully hereinafter in the detailed explanation of FIGS. 4 through 7, fully-assembled test devices were tested by applying a 0.1 volt potential across the two isolated interdigited electrodes in the microelectrode assembly and measuring the increase in conductivity of the film or layer of conducting polymer as the conducting polymer is doped by the dopant compound generated in the reaction zone. It was found that a linear change in conductivity of the film or layer of conducting polymer results from the enzymatic oxidation of glucose in standardized glucose solutions including from 25 to 500 mg/dL glucose and of 30 to 50 mM/L potassium iodide. Ultimately, the iodide ion was oxidized to molecular iodine that dopes the film or layer of conducting polymer, and accordingly, increases the conductivity of the conducting polymer film such that currents in the range of from 1 to 5 μamps were observed. In general, the plots presented in FIG. 4 illustrate the results for glucose assays of standardized glucose solutions. The plots in FIGS. 6 and the plot in FIG. 7 were identically derived, except the glucose oxidase activity in the reaction zone was increased slightly from 85 U/mg to 118 U/mg of casting solution. In FIGS. 5 and 7, a dose response plot is generated in each experiment by polling the current at 10 seconds.

In particular, the dose response plots graphed in FIG. 4 illustrate the results of assays for glucose utilizing the method and device of the present invention. Standardized glucose solutions including from 25 mg/dL to 500 mg/dL, and further including 30 mM potassium iodide, were assayed by a test device 10 as illustrated in FIG. 1. Initially, it can be observed that the greater the concentration of glucose in solution, the greater the initial change in conductivity, and the greater the total change in conductivity, of the film or layer of conducting polymer. In addition, it also is observed that the change in conductivity of the film or layer of conducting polymer is greatest when the percentage amount of dopant compound in the conducting polymer layer is relatively low, i.e. at the early stages of the glucose-glucose oxidase interaction, such as within about 30 seconds, and especially within about 15 seconds, of the onset the glucose-glucose oxidase interaction. As a result, the supply of ambient oxygen has not been significantly depleted.

Therefore, the most sensitive measurement for the change in conductivity of the conducting polymer film is made within approximately the first 30 seconds, and preferably within approximately the first 10 seconds, after the test sample contacts the reaction zone of the test device. The change in conductivity after the first 25 seconds does not appreciably increase because of ambient oxygen supply depletion or because the amount of glucose in the reaction zone, usually less than about 1% of the glucose in the test sample, has interacted with the enzymes and the dopant compound precursor.

It should be understood that only a small amount of the available glucose present in the test sample is actually converted to eventually generate molecular iodine, and that the amount of glucose in the test sample is determined from the initial reaction rate between the glucose and the enzymes to generate molecular iodine. In addition, in a commercial test device, the iodide ion is included in the reaction zone with the enzymes and other necessary reagents rather than adding the iodide ion to the glucose-containing test sample.

The graph plotted in FIG. 5 illustrates the linear response of the change in conductivity of the layer of conducting polymer to the amount of glucose in the test sample. In each assay, the conductivity of the layer of conducting polymer was measured 10 seconds after the glucose-containing sample contacted the reaction zone of the test device. The linear relationship illustrated in FIG. 5 shows that a test sample including an unknown amount of glucose can be assayed by the device and method of the present invention. For example, the small test sample is introduced into the test device. Then, ten seconds after the test sample contacts the reaction zone, the conductivity of the layer of conducting polymer is measured. From a linear graph as presented in FIG. 5 and derived from standardized glucose solutions, the measured conductivity of the layer of conducting polymer can be correlated to the amount of glucose in the test sample. It has been found that the most sensitive and accurate assays are achieved when the conductivity is measured from about 5 seconds to about 30 seconds after the test sample contacts the reaction zone.

Figure 6:
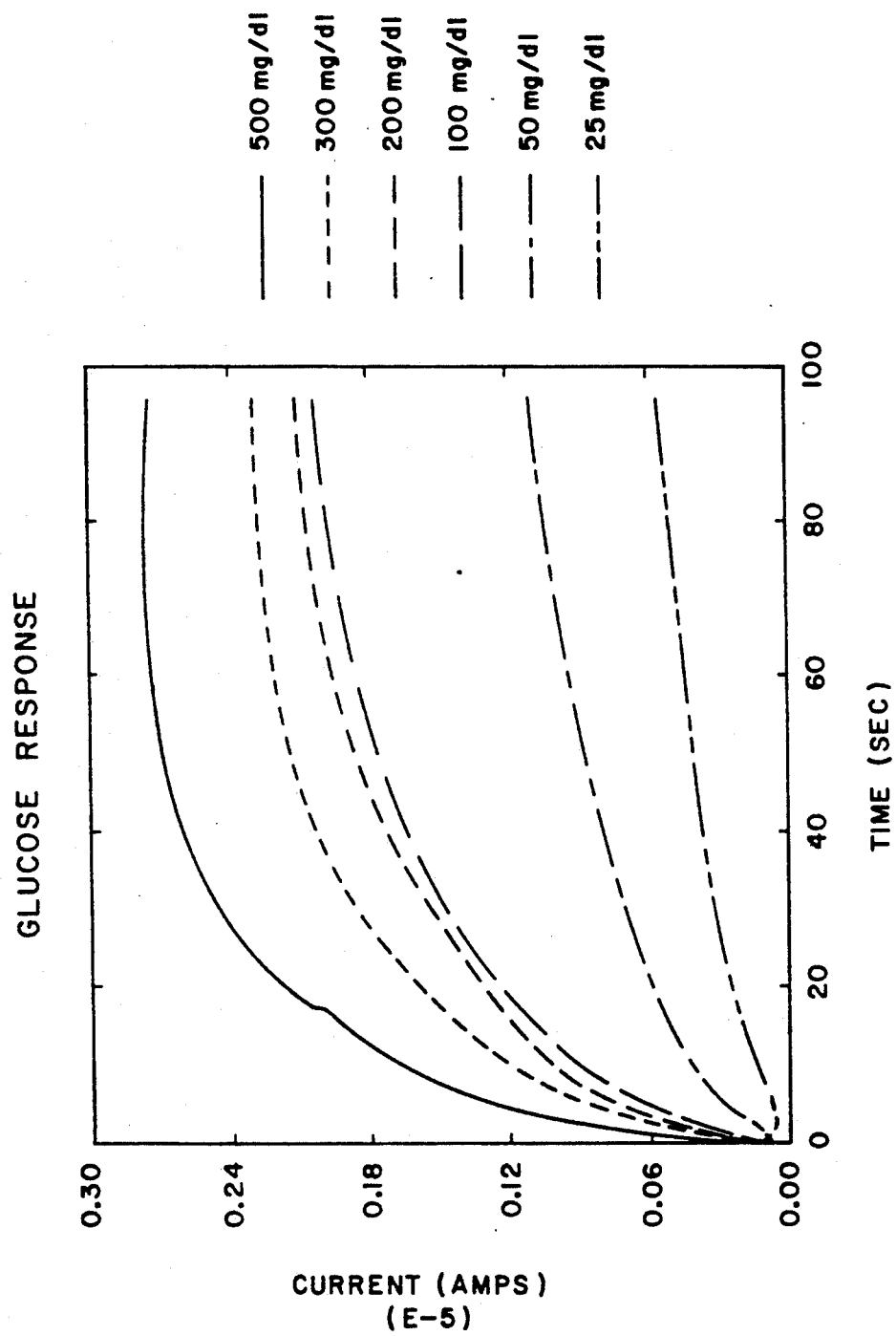
FIG. 6 is another dose response plot of current (amps) vs. time (seconds) for assays of standardized solutions including 30 mM potassium iodide and either 25, 50, 100, 200, 300 or 500 mg/dL of glucose assayed by the method and conductive sensor of the present invention.
Figure 7:
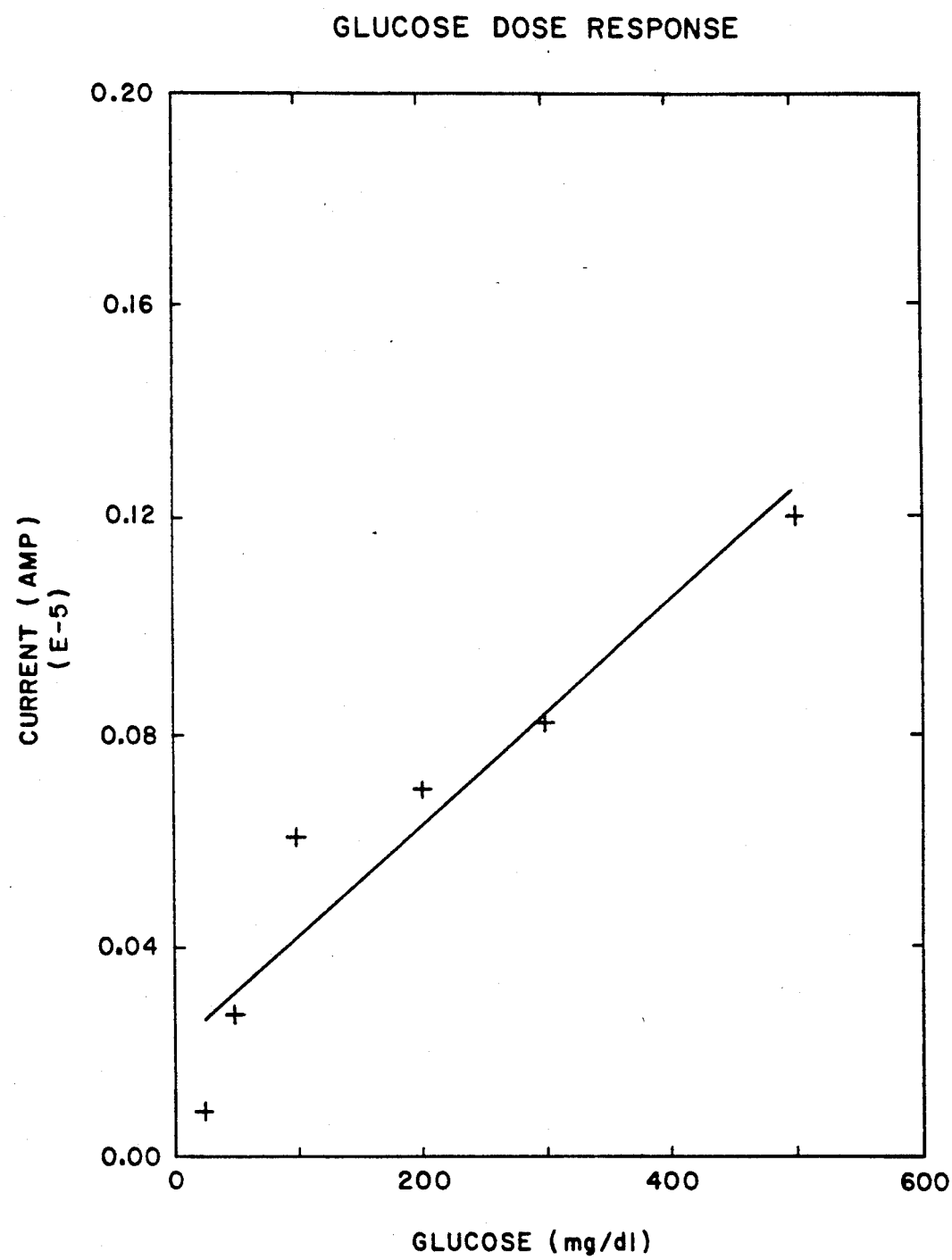
FIG. 7 is a plot of current (amps at 10 seconds) vs. glucose concentration (mg/dL) showing the linear relationship between the concentration of glucose in a standardized test sample and conductivity of the layer of conducting polymer exhibited by a conductive sensor of the present invention.

The plots in FIGS. 6 and 7 show essentially identical results obtained when the amount of glucose oxidase in the casting solution, and hence in the reaction zone is increased. The greatest change in conductivity is observed in the first 30 seconds, and especially in the first 15 seconds, of the reaction zone interaction (FIG. 6) and the linearity of the measured conductivity of the layer of conducting polymer to the concentration of glucose in the test sample is maintained (FIG. 7). Hence the method and device of the present invention provide a fast, economical, sensitive and accurate assay of a liquid test sample including glucose in amounts as low as 0 mg/dL and up to 600 mg/dL.

In accordance with another important feature of the present invention, another test device was prepared by the above-described method and included a semipermeable membrane, i.e. a test device 40 of FIG. 3. This test device accurately assayed standardized glucose solutions including from 5 mg/dL to 500 mg/dL glucose. The standardized glucose solutions further included iodide ions. As discussed above and illustrated below, in a test device of the present invention, the iodide ions preferably are included in the reaction zone of the conductive sensor in an amount ranging from about 50 mM to about 500 mM. The conductivity of the film or layer of conducting polymer in the detection zone was measured at an applied voltage of 0.1 V (volt), and electrical currents the range of from 0.1 μamp (microamp) to 5 μamp were found as typical.

As will be demonstrated more fully hereinafter in the detailed explanation of FIGS. 8 and 9, fully-assembled test devices were tested by applying a 0.1 volt potential across the two isolated interdigited electrodes in the microelectrode assembly and measuring the increase in conductivity of the film or layer of conducting polymer as the conducting polymer is doped by the dopant compound generated in the reaction zone. It was found that a linear change in conductivity of the film or layer of conducting polymer results from the enzymatic oxidation of glucose in standardized glucose solutions including from 5 mg/dL to 500 mg/dL glucose and 150 mM/L potassium iodide. Ultimately, the iodide ion was oxidized to molecular iodine that dopes the film or layer of conducting polymer, and accordingly, increases the conductivity of the conducting polymer film such that currents in the range of from 1 to 5 μamps were observed.

In particular, in these assays, the test device included a conductive sensor 40 wherein the reaction zone 44 included chitosan as the hydratable matrix material. In this embodiment, a 3% by weight aqueous solution of shellfish chitosan, available from PROTAN, INC., Commack, N.Y., first was prepared. Then a sufficient amount of glucose oxidase and peroxidase was added to the 3% chitosan solution to provide a chitosan solution that includes 10 mg/ml (milligrams per milliliter) each of glucose oxidase and perioxidase. This chitosan solution then was cast over a layer of polyoctylthiophene, as previously described.

After allowing chitosan layer to dry sufficiently to provide the reaction zone 44, a semipermeable membrane 42 was cast over the chitosan layer. The semipermeable membrane 42 was applied by casting an aqueous solution including about 75% by weight of the elastomer, Dow Corning Latex 3-5035, available from Dow Corning Corporation, Midland, Mich., and about 0.1% by weight OLIN SURFACTANT 10G onto the chitosan-based reaction zone 44. After drying the film of elastomer-based semipermeable membrane 42, a conductive sensor 40 was provided to assay a test sample for glucose.

Figure 8:
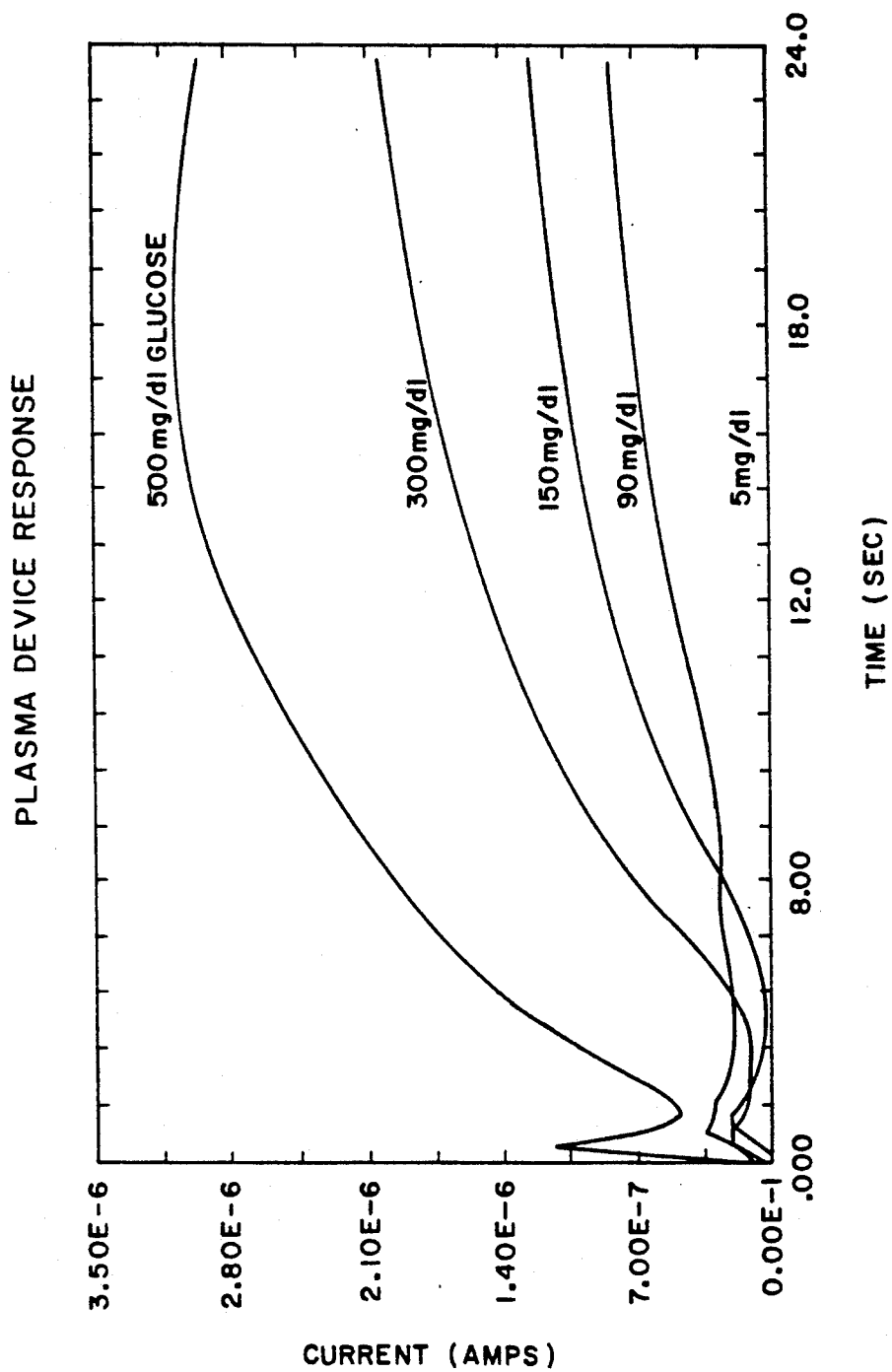
FIG. 8 is a dose response plot of current (amps) vs. time (seconds) for assays of standardized solutions including 150 mM potassium iodide and either 5, 90, 150, 300 or 500 mg/dL of glucose assayed by the method and preferred embodiment of the conductive sensor of the present invention.
Figure 9:
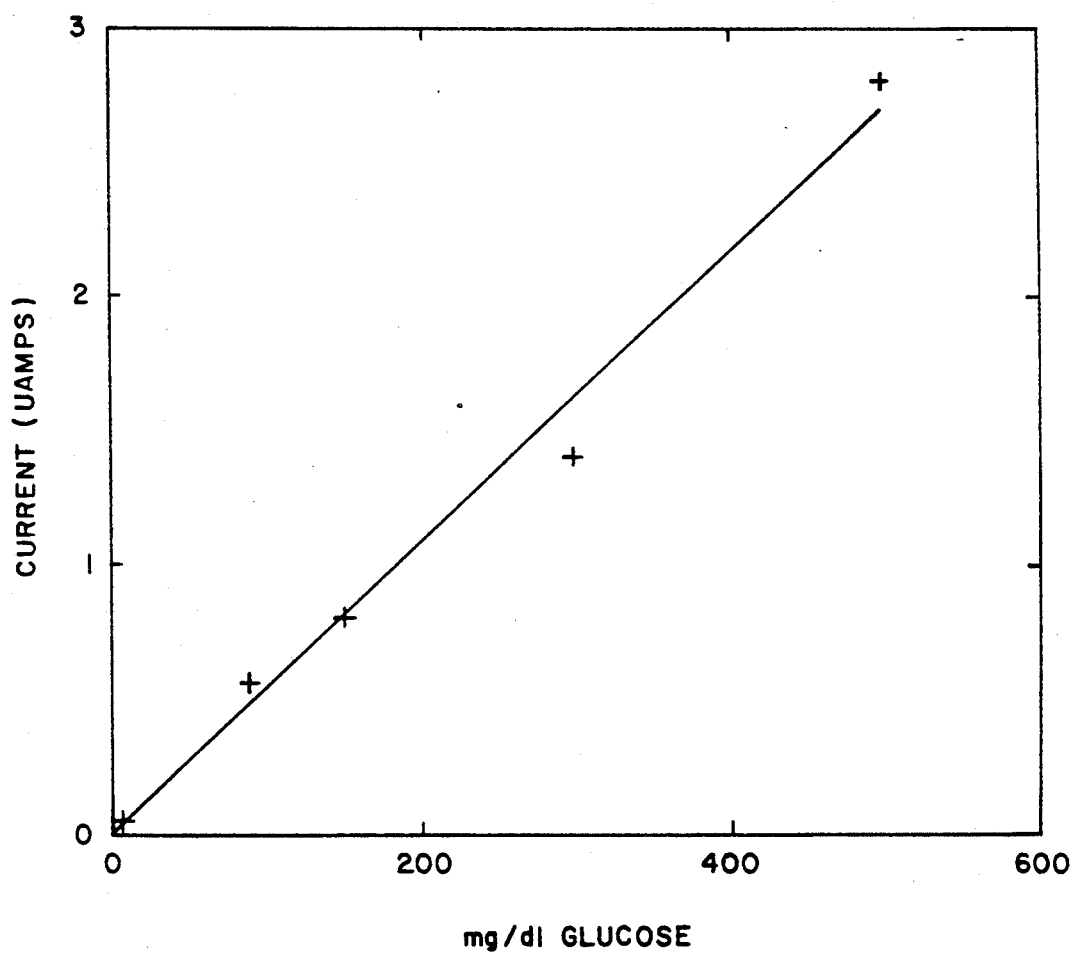
FIG. 9 is a plot of current (microamps at 10 sec.) vs. glucose concentration (mg/dL) showing the linear relationship between the concentration of glucose in a standardized test sample and conductivity of the layer of conducting polymer exhibited by a conductive sensor of the present invention.

In general, the plots presented in FIGS. 8 and 9 illustrate the results of glucose assays of standardized glucose solutions using a conductive sensor 40 of FIG. 3. In both FIGS., a dose response plot is generated in each experiment by polling the current at 10 seconds.

In particular, the dose response plots graphed in FIG. 8 illustrate the results of assays for glucose on standardized glucose solutions including from 5 mg/dL to 500 mg/dL glucose, and further including 30 mM potassium iodide. Initially, it can be observed that the greater the concentration of glucose in solution, the greater the initial change in conductivity, and the greater the total change in conductivity, of the film or layer of conducting polymer. In addition, it also is observed that the change in conductivity of the film or layer of conducting polymer is greatest when the percentage amount of dopant compound in the conducting polymer layer is relatively low, i.e. at the early stages of the glucose-glucose oxidase interaction, such as within about 25 seconds, and especially within about 12 seconds, of the onset the glucose-glucose oxidase interaction. Therefore, the most sensitive measurement for the change in conductivity of the conducting polymer film is made within approximately the first 30 seconds, and preferably within approximately the first 10 seconds, after the test sample contacts the reaction zone of the test device.

The graph plotted in FIG. 9 illustrates the linear response of the change in conductivity of the layer of conducting polymer to the amount of glucose in the test sample. In each assay, the conductivity of the layer of conducting polymer was measured 10 seconds after the glucose-containing sample contacted the reaction zone of the test device. The linear relationship illustrated in FIG. 9 shows that a test sample including an unknown amount of glucose can be assayed by the device and method of the present invention.

Hence the device of the present invention depicted in FIG. 3 provides a fast, economical, sensitive and accurate assay of a liquid test sample including glucose in amounts as low as 0 mg/dL and up to 600 mg/dL.

To demonstrate that a conductive sensor of the present invention can accurately assay a test sample for glucose when the iodide ion is included in the reaction zone of the conductive sensor the following assays were performed using a test device including a conductive sensor 40 as depicted in FIG. 3. It has been found that the iodide ion is most easily incorporated into the reaction zone 44 in the form of a tetraalkylammonium iodide, wherein the alkyl group includes from one to about four carbon atoms. Preferably, the tetraalkylammonium iodide is tetraethylammonium iodide. However, the tetramethyl, tetrapropyl and tetrabutyl iodides also can be used. Similarly, potassium iodide, lithium iodide, sodium iodide and other water-soluble iodide salts can be used as the source of iodide ions in the reaction zone. The iodide salt is included in the casting solution used to form the reaction zone in a concentration ranging from about 50 mM to about 500 mM, and preferably in the range of from about 75 mM to about 300 mM.

Figure 10:
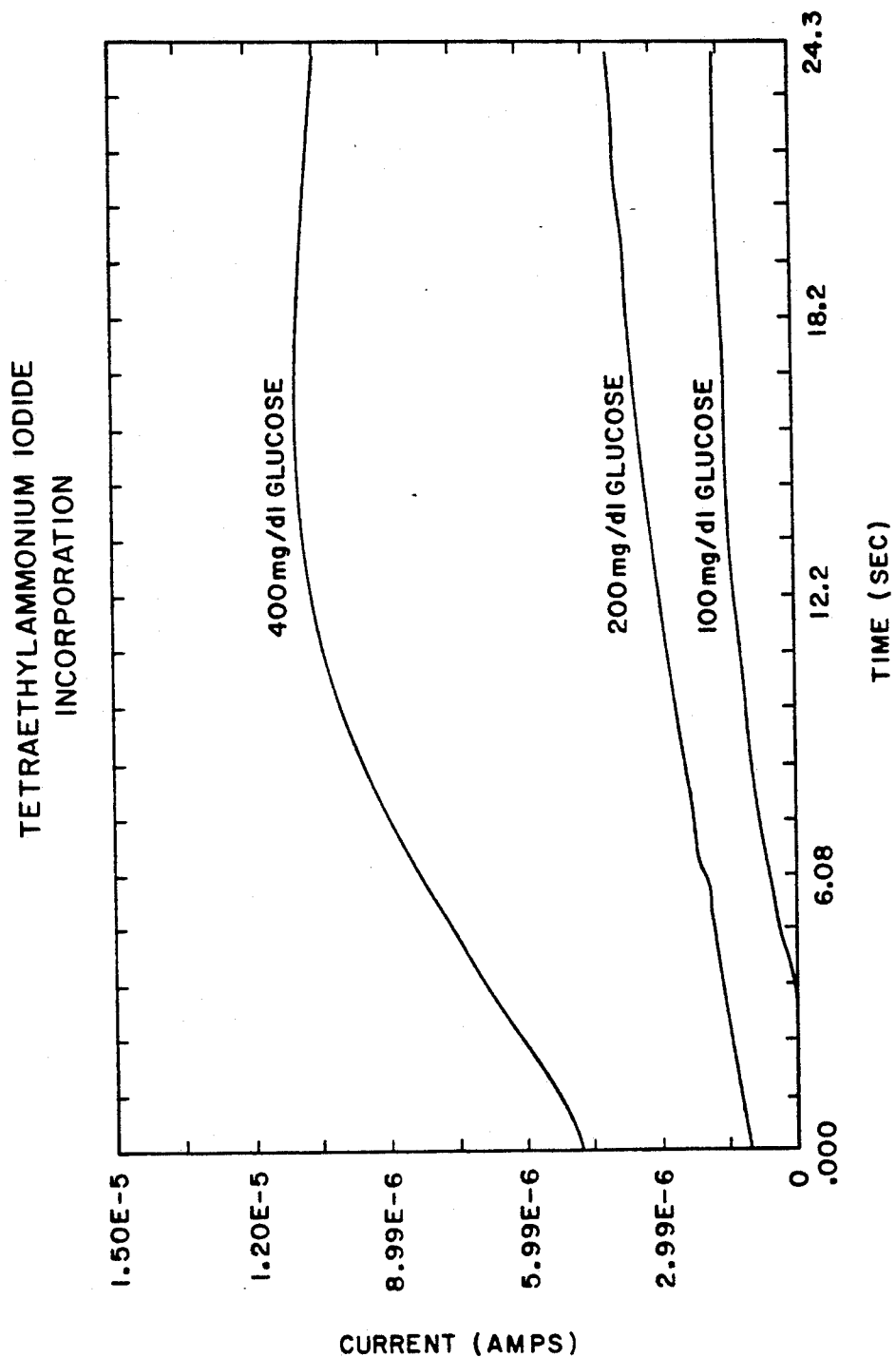
FIG. 10 is a dose response plot of current (amps) vs. time (seconds) for assays of standardized solutions including 100 mM tetraethylammonium iodide and either 100, 200 or 400 mg/dL of glucose assayed by the method and conductive sensor of the present invention.

FIG. 10 includes the dose response plots for glucose assays utilizing a conductive sensor 40 of FIG. 3 wherein tetraethylammonium iodide was included in a chitosan-based reaction zone 44 at a concentration of about 100 mM. In this experiment, the conductive sensor was slightly modified in that a second chitosan-based film, including the tetraethylammonium iodide, was applied over a first chitosan-based film that included the glucose oxidase and the peroxidase. Although this particular reaction 44 included two distinct chitosan films, the iodide salt, glucose oxidase and peroxidase can be included in a single chitosan, or gelatin, film. A semipermeable membrane 42, comprising a silicone-based elastomer, was cast over the chitosan-based film including the tetraethylammonium iodide. The above-described test device was used to assay standardized solutions including 100 mg/dL, 200 mg/dL and 400 mg/dL of glucose. The results of the glucose assay are illustrated in FIG. 10, showing that the device analyzes for glucose within about 15 seconds.

Several enzyme-based assays involve the generation of hydrogen peroxide as a reaction product. As described above for glucose, the generation of hydrogen peroxide in the glucose-glucose oxidase interaction provides a substrate for the peroxidase enzyme to generate the molecular iodine dopant compound. The molecular iodine then dopes the film or layer of conducting polymer, and the amount of glucose in the test sample is determined from the change in conductivity of the conducting polymer layer. However, in addition to glucose oxidase, oxidase enzymes that employ oxygen as a mediator, and therefore produce hydrogen peroxide upon interaction with the appropriate substrate include, but are not limited to:

cholesterol oxidase,
aryl-alcohol oxidase,
L-gluconolactone oxidase,
galactose oxidase,
pyranose oxidase,
L-sorbase oxidase,
pyridoxin 4-oxidase,
alcohol oxidase,
L-2-hydroxyacid oxidase,
pyruvate oxidase,
oxalate oxidase,
glyoxylate oxidase,
dihydro-orotate oxidase,
lathosterol oxidase,
choline oxidase,
glycolate oxidase,
glycerol-3-phosphate oxidase,
xanthine oxidase,
sarcosine oxidase,
N-methylamino-acid oxidase,
$N^6$-methyl-lysine oxidase,
6-hydroxyl-L-nicotine oxidase,
6-hydroxy-D-nicotine oxidase,
nitroethane oxidase,
sulphite oxidase,
thiol oxidase,
cytochrome c oxidase,
Pseudomonas cytochrome oxidase,
ascorbate oxidase,
o-aminophenol oxidase, and
3-hydroxyanthranilate oxidase.

As a result, in accordance with the device and method of the present invention, conductive sensors for a particular predetermined analyte can be designed utilizing the appropriate oxidase enzyme in the same device and method described above the assay of glucose. However, it should be understood, that for the embodiment illustrated in FIG. 3, the semipermeable membrane can inhibit the passage of certain higher molecular weight compounds, like cholesterol, through the semipermeable membrane. Therefore, the conductive sensor of the present invention embodied in FIG. 3 may not be suitable in assays for higher molecular weight analytes, like cholesterol. In general however, as long as the predetermined analyte exhibits a diffusion constant of at least about $1 \times 10^{-9}$ cm$^2$/sec through the semipermeable membrane, then the presence or concentration of the predetermined analyte can be determined by the method and device of the present invention.

The primary features relating to the test device and method of the present invention have been repeatedly observed. The new and unexpected results arising from the method of the present invention provides test devices designed to assay a liquid test sample for a predetermined analyte capable of interacting with oxygen and an oxidase enzyme.

From the foregoing, it is seen that the present invention is well adapted to attain all of the objects hereinabove set forth. The method and device have the advantages of convenience, simplicity, relative economy, disposability, sensitivity and accuracy. Among the advantages of the present invention is that the device operates nonoptically; has excellent shelf life stability; can be constructed at relatively low cost; can be reproducibly manufactured by semiconductor processing techniques; has a great degree of flexibility with respect to format; requires a small, noninvasive amount of sample; and can be constructed to have a relatively small size.

For example, it is envisioned that a test device of the present invention is an economical, miniaturized, disposable device. Each component in every embodiment of the present invention can be manufactured in a batch processing technique. In addition, the microelectrode assembly can be manufactured by a number of techniques well-known in the art utilizing a silicon, ceramic, glass or plastic base. Furthermore, the conductive sensor is stable because the method and device utilize an undoped, reduced layer conducting polymer, as opposed to a less stable, oxidized conducting polymer utilized in most prior art conductive sensors.

Although the present invention is primarily directed to assaying liquid media for various clinically significant substances or constituents in biological fluids, such as urine and blood, including lysed or unlysed blood, blood plasma and blood serum, it should be understood that the device and method of the present invention are useful for assays of nonbiological fluids, including swimming pool water, wines, etc.

It will be understood that the present disclosure has been made only by way of preferred embodiment and that numerous changes in details of construction, combination, and arrangement of parts can be resorted to without departing from the spirit and scope of the invention as hereunder claimed.

We claim:

1. A conductive sensor for assaying a test sample for the presence or concentration of glucose, said conductive sensor comprising:
    a) a semipermeable membrane capable of effectively separating cellular material and interfering components from a test sample and capable of allowing glucose to permeate through the semipermeable membrane at a uniform rate said semipermeable membrane having a diffusion constant for glucose in the range of from about $1 \times 10^{-9}$ cm²/sec to about $5 \times 10^{-8}$ cm²/sec and a diffusion constant for molecular oxygen in the range of from about $5 \times 10^{-7}$ cm²/sec to about $5 \times 10^{-6}$ cm²/sec and having a thickness of from about $3\mu$ to about $15\mu$;
    b) a layer of a host matrix in contact with the semipermeable membrane and permeable to the glucose, said hose matrix layer having homogeneously incorporated therein glucose oxidase, a compound having peroxidase activity and a dopant compound precursor, wherein the glucose, the glucose oxidase, the compound having peroxidase activity and the dopant compound precursor interact to form a dopant compound;
    c) a layer of a polymer in its reduced form which demonstrates an increase in electrical conductivity when it is converted to its oxidized form in contact with the host matrix layer such that at least a portion of the dopant compound generated in the host matrix layer migrates to and oxidatively dopes the polymer layer to thereby increase the conductivity of this layer; and
    d) means operatively connected to the polymer layer for measuring a change in conductivity of polymer layer.

2. The conductive sensor of claim 1 wherein the means for measuring the change in conductivity of the polymer layer comprises a microelectrode assembly in contact with the polymer layer, said microelectrode assembly constructed to sense the change in conductivity of the polymer layer in response to the oxidative doping of the polymer layer by the dopant compound.

3. The conductive sensor of claim 2 wherein the microelectrode assembly comprises an interdigited pair of metal electrodes having an insulating spacing of from about $10\mu$ to about $300\mu$.

4. The conductive sensor of claim 1 wherein the compound having peroxidase activity is horseradish peroxidase, lactoperoxidase, microperoxidase or combinations thereof.

5. The conductive sensor of claim 1 wherein the host matrix layer has a thickness of from about $0.1\mu$ to about $10\mu$ and comprises gelatin, chitosan, silk fibroin, collagen, poly(2-hydroxyethylmethacrylate), polyacrylamide or combinations thereof.

6. The conductive sensor of claim 1 wherein the dopant compound precursor is iodide ion, said iodide ion incorporated into the host matrix layer as an iodide salt selected from the group consisting of lithium iodide, sodium iodide, potassium iodide, a tetraalkylammonium iodide wherein the alkyl group includes from one to about four carbon atoms, and combinations thereof.

7. The conductive sensor of claim 6 wherein the compound having peroxidase activity is a molybdenum(VI) transition metal catalyst.

8. The conductive sensor of claim 6 wherein the polymer layer has a thickness of less than 10,000 Å and comprises a poly(alkylthiophene), a polythiophene, a poly(thienylene vinylene), a poly(furylene vinylene), a polypyrrole, a polyfuran, a polyaniline or a combination thereof.

9. The conductive sensor of claim 8 wherein the poly(alkylthiophene) is a poly(3-alkylthiophene) wherein the alkyl group includes from about four carbon atoms to about 20 carbon atoms.

10. The conductive sensor of claim 1 wherein the semipermeable membrane has a thickness in the range of from about $5\mu$ to about $10\mu$.

11. The conductive sensor of claim 1 wherein the semipermeable membrane has a thickness in the range of from about $6\mu$ to about $8\mu$.

12. The conductive sensor of claim 1 wherein the semipermeable membrane is an elastomeric compound.

13. The conductive sensor of claim 1 wherein the semipermeable membrane is a silicone-containing elastomer.

14. The conductive sensor of claim 1 wherein the semipermeable membrane comprises polypropylene, nylon, polycarbonate, polyurethane or a combination thereof.

15. The conductive sensor of claim 1 wherein the glucose oxidase and compound peroxidase having activity are in a first matrix layer and the dopant compound precursor is in a second matrix layer immediately adjacent to the first matrix layer.

16. The conductive sensor of claim 15 wherein the first matrix layer and the second matrix layer are comprised of chitosan.

17. The conductive sensor of claim 16 wherein the dopant compound precursor is tetraethylammonium iodide.

18. The conductive sensor of claim 1 wherein the host matrix comprises a first layer containing the glucose oxidase and compound peroxidase having activity and a second layer immediately adjacent to the first layer which contains the dopant compound precursor material.

19. The conductive sensor of claim 18 wherein the first and second layers of the host matrix are comprised of chitosan.

20. The conductive sensor of claim 19 wherein the dopant compound precursor is tetraethylammonium iodide.

21. A conductive sensor for assaying a biological fluid for the presence or concentration of a predetermined analyte, said predetermined analyte capable of interacting with an oxidase enzyme, and said conductive sensor comprising:

a) an elastomer-based semipermeable membrane having a thickness of from about $5\mu$ to about $10\mu$, said elastomer-based semipermeable membrane capable of effectively separating cellular material and interfering components from a biological fluid and capable of allowing a predetermined analyte to permeate through the elastomer-based semipermeable membrane at a uniform rate;

b) a layer of a host matrix, comprising gelatin, chitosan or a combination thereof and having a thickness of from about $0.2\mu$ to about $5\mu$, in contact with the semipermeable membrane, said host matrix layer permeable to the predetermined analyte and said host matrix layer having homogeneously incorporated therein an oxidase enzyme capable of interacting with the predetermined analyte, a peroxidase enzyme or a molybdenum(VI) transition metal catalyst, and iodide ion, wherein the predetermined analyte, the oxidase enzyme, the peroxidase enzyme or the molybdenum(VI) catalyst, and the iodide ion interact to generate molecular iodine;

c) a layer of a conducting polymer having a thickness of from about 100 Å to about 2000 Å in contact with the host matrix layer such that at least a portion of the molecular iodine generated in the host matrix layer migrates to and oxidatively dopes the conducting polymer layer; and d) a microelectrode assembly in contact with the conducting polymer layer, said microelectrode assembly adapted to sense a change in conductivity of the conducting polymer layer in response to the oxidative doping of the conducting polymer layer by the molecular iodine.

* * * * *